United States Patent
Mitani et al.

(10) Patent No.: US 8,568,755 B2
(45) Date of Patent: Oct. 29, 2013

(54) FUNGICIDAL COMPOSITION AND METHOD FOR CONTROLLING NOXIOUS FUNGI

(75) Inventors: Shigeru Mitani, Osaka (JP); Shintaro Tsukuda, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 376 days.

(21) Appl. No.: 12/740,121

(22) PCT Filed: Oct. 20, 2008

(86) PCT No.: PCT/JP2008/069392
§ 371 (c)(1),
(2), (4) Date: Apr. 28, 2010

(87) PCT Pub. No.: WO2009/060734
PCT Pub. Date: May 14, 2009

(65) Prior Publication Data
US 2010/0255116 A1    Oct. 7, 2010

(30) Foreign Application Priority Data

Nov. 5, 2007  (JP) ................................ 2007-287699

(51) Int. Cl.
*A01N 25/00*    (2006.01)

(52) U.S. Cl.
USPC ........................................................ 424/405

(58) Field of Classification Search
None
See application file for complete search history.

(56) References Cited

U.S. PATENT DOCUMENTS

| | | | |
|---|---|---|---|
| 7,439,366 B2 | 10/2008 | Nakamura et al. | |
| 7,683,096 B2 | 3/2010 | Nakamura et al. | |
| 2008/0318779 A1 | 12/2008 | Nakamura et al. | |
| 2010/0093707 A1 | 4/2010 | Nakamura et al. | |

FOREIGN PATENT DOCUMENTS

| | | |
|---|---|---|
| EP | 1 256 569 | 11/2002 |
| EP | 1 428 817 | 6/2004 |
| JP | 2007 210924 | 8/2007 |
| WO | 2006 016708 | 2/2006 |
| WO | WO 2006016708 A1 * | 2/2006 |
| WO | 2007 069777 | 6/2007 |

OTHER PUBLICATIONS

U.S. Appl. No. 12/095,517, filed May 30, 2008, Nakamura, et al.

* cited by examiner

*Primary Examiner* — Anand Desai
*Assistant Examiner* — Melissa Mercier
(74) *Attorney, Agent, or Firm* — Oblon, Spivak, McClelland, Maier & Neustadt, L.L.P.

(57) ABSTRACT

A fungicidal composition is provided. A fungicidal composition comprising synergistically effective amounts of (a) a carboxylic acid amide derivative of the formula (I) or its salt: wherein B is a heterocyclic group which may be substituted; each of $R_1$ and $R_2$ which are independent of each other, is alkyl; X is halogen, alkyl or alkoxy; and n is an integer of from 0 to 5, and (b) at least one fungicidal compound selected from the group consisting of an azole compound, an anilinopyrimidine compound, a triazolopyrimidine compound, a strobilurin compound, an N-halogenothioalkyl compound, a pyridinamine compound, a bicarbonate, an inorganic sulfur compound, a dithiocarbamate compound, an organic chlorine compound, a dicarboxyimide compound, an amine compound, a phenylpyrrole compound, a benzophenone compound, a dinitrobenzene compound, a piperidine compound, a morpholine compound, etc.

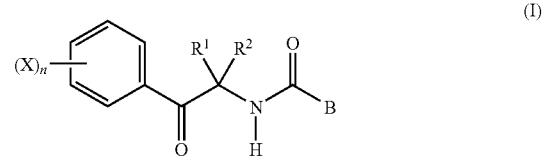

3 Claims, 1 Drawing Sheet

FUNGICIDAL COMPOSITION AND METHOD FOR CONTROLLING NOXIOUS FUNGI

TECHNICAL FIELD

The present invention relates to a fungicidal composition having effects for controlling various noxious fungi remarkably improved, and a method for controlling noxious fungi.

BACKGROUND ART

Patent Documents 1, 2 and 3 disclose that compounds included in the formula (I) given hereinafter are useful as fungicides, and it is disclosed that they may be used in combination or as mixed with other fungicides, as the case requires. However, it is not known that the compound of the formula (I) presents a distinctly superior fungicidal effect when it is used in combination with another specific fungicide in a synergistically effective amount. Further, Patent Documents 4 and 5 disclose that compounds included in the formula (I) given hereinafter are useful as pesticides such as nematicidal agents.

Patent Document 1: WO06/016708
Patent Document 2: WO07/069,777
Patent Document 3: JP-A-2007-210924
Patent Document 4: EP1256569A
Patent Document 5: EP1428817A

DISCLOSURE OF THE INVENTION

Problem to be Solved by the Invention

The carboxylic acid amide derivatives of the formula (I) given hereinafter sometimes show practically no adequate controlling effects against certain diseases, such that their controlling effects are not adequate against certain noxious fungi depending upon the concentration range or the application site, the residual effects are relatively short, or the resistance against rain is weak.

Means to Solve the Problem

The present inventors have conducted a research to solve the above problem and as a result, have found that particularly when a carboxylic acid amide derivative of the formula (I) given hereinafter and a certain specific fungicidally effective compound are used as mixed, it is possible to obtain unexpectedly excellent fungicidal activities as compared with a case where the respective compounds are used independently. Thus, the present invention has been accomplished on the basis of this discovery. Namely, the present invention provides a fungicidal composition comprising synergistically effective amounts of (a) a carboxylic acid amide derivative of the formula (I) or its salt:

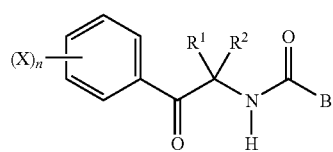

(I)

wherein B is a heterocyclic group which may be substituted by Y; each of $R^1$ and $R^2$ which are independent of each other, is $C_{1-12}$ alkyl; X is halogen, $C_{1-12}$ alkyl or $C_{1-12}$ alkoxy; Y is halogen, $C_{1-12}$ alkyl or $C_{1-12}$ haloalkyl; and n is an integer of from 0 to 5; and (b) at least one fungicidal compound selected from the group consisting of an azole compound, an anilinopyrimidine compound, a triazolopyrimidine compound, a strobilurin compound, an N-halogenothioalkyl compound, a pyridinamine compound, a bicarbonate, an inorganic sulfur compound, a dithiocarbamate compound, an organic chlorine compound, a dicarboxyimide compound, an amine compound, a phenylpyrrole compound, a benzophenone compound, a piperidine compound, a dinitrobenzene compound, a morpholine compound, a cyanoacetamide compound, a phosphorous acid compound, an organophosphorus compound, a carboxamide compound, a quinoline compound, a copper compound, a carbamate compound, an antibiotic, a guanidine compound, an oxime ether compound, a 4-quinolinol derivative compound, a cyanomethylene compound, a quinazolinone compound and a benzoylpyridine compound. Further, the present invention provides a method for controlling noxious fungi, which comprises applying a fungicidally effective amount of such a fungicidal composition to noxious fungi or to a site where they grow. Further, the present invention provides a method for controlling noxious fungi, which comprises applying a fungicidally effective amount of (a) the carboxylic acid amide derivative of the formula (I) or its salt, and a fungicidally effective amount of (b) the fungicidal compound, to noxious fungi or to a site where they grow.

Effects of the Invention

The fungicidal composition comprising synergistically effective amounts of (a) the carboxylic acid amide derivative of the formula (I) or its salt, and (b) the fungicidal compound (hereinafter referred to simply as the composition of the present invention) is capable of controlling, particularly at low dose, various fungi such as Oomycetes, Ascomycetes, Basidiomycetes or Deuteromycetes, and capable of effectively controlling various plant diseases thereby caused. Unexpectedly, their fungicidal activities exhibit an effect more than a mere additive effect of their respective individual fungicidal activities, i.e. a synergistic fungicidal activity. Thus, the composition of the present invention containing synergistically effective amounts of (a) the carboxylic acid amide derivative of the formula (I) or its salt, and (b) the fungicidal compound, can be applied in a low dose as compared with a case where the respective agents are used independently, and accordingly, it is effective also to reduce the environmental load at the application site or its surroundings. Further, the fungicidal spectrum can be enlarged, and further, the fungicidal activities will last over a long period of time.

BEST MODE FOR CARRYING OUT THE INVENTION

Figure 1:
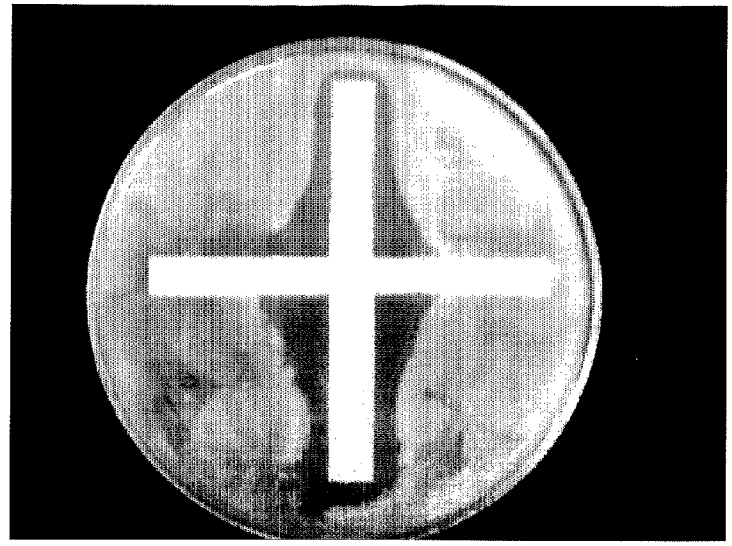
FIG. 1 is a photograph showing the results of the test on antimicrobial activity against gray mold pathogen in Test Example 7.

In a case where in the above formula (I), the number of substituents represented by X is more than one, such substituents may be the same or different. The substation number of Y as substituents contained in B may be one or more, and in the case of more than one, such substituents may be the same or different.

The heterocyclic moiety of the substituent represented by B in the above formula (I) is preferably a 3- to 6-membered heterocyclic ring containing from 1 to 4 atoms of at least one type selected from the group consisting of an oxygen atom, a sulfur atom and a nitrogen atom, and it may, for example, be a 3-membered heterocyclic ring such as oxiranyl; a 5-membered heterocyclic ring such as furyl, tetrahydrofuryl, thienyl, pyrrolyl, pyrrolinyl, pyrrolidinyl, dioxolanyl, oxazolyl, isoxazolyl, thiazolyl, isothiazolyl, imidazolyl, imidazolinyl, imidazolidinyl, pyrazolyl, pyrazolinyl, pyrazolidinyl, triazolyl, oxadiazolyl, thiadiazolyl or tetrazolyl; or a 6-membered heterocyclic ring such as pyranyl, pyridyl, piperidinyl, dioxanyl, oxazinyl, morpholinyl, thiazinyl, pyridazinyl, pyrimidinyl, pyrazinyl, piperazinyl, triazinyl, dihydrooxathiinyl, dihydrooxooxathiinyl, dihydrodioxooxathiinyl, dihydropyranyl or dihydrothiinyl. Among them, more preferred is a 5- or 6-membered heterocyclic group containing one or two atoms of at least one type selected from the group consisting of an oxygen atom, a sulfur atom and a nitrogen atom, and most preferred is pyridyl, thienyl or pyrazolyl. Further, a specific example of the substituent represented by B may, for example, be 3-trifluoromethyl-2-pyridyl, 3-methyl-2-thienyl or 1-methyl-3-trifluoromethyl-4-pyrazolyl.

The alkyl or alkyl moiety in the above formula (I) may be $C_{1-12}$ linear or branched one, such as methyl, ethyl, n-propyl, isopropyl, n-butyl, isobutyl, tert-butyl, n-pentyl, 2-pentyl, n-hexyl, 2-hexyl, 3-hexyl, heptyl, octyl, nonyl, decanyl, undecanyl or dodecanyl.

The halogen or the halogen as a substituent in the above formula (I) may be an atom of fluorine, chlorine, bromine or iodine. The number of halogens as substituents, may be one or more, and in the case of more than one, such halogens may be the same or different. Further, such halogens may be substituted at any positions.

The salt of the carboxylic acid, amide derivative of the above formula (I) may be any salt so long as it is agriculturally acceptable. For example, it may be an alkali metal salt such as a sodium salt or a potassium salt; an alkaline earth metal salt such as a magnesium salt or a calcium salt; an inorganic acid salt such as a hydrochloride, a perchlorate, a sulfate or a nitrate; or an organic acid salt such as an acetate or a methane sulfonate.

The carboxylic acid amide derivative of the above formula (I) has various isomers such as optical isomers or geometrical isomers, and the present invention includes both isomers and mixtures of such isomers. Further, the present invention also includes various isomers other than the above isomers within the common knowledge in the technical field concerned. Further, depending upon the types of isomers, they may have chemical structures different from the above formula (I), but they are within the scope of the present invention, since it is obvious to those skilled in the art that they are isomers.

The carboxylic acid amide derivative of the above formula (I) or its salt may be produced by the process disclosed in the above-mentioned Patent Document 1, 2 or 3.

Among the carboxylic acid amide derivatives of the above formula (I), preferred ones will be listed below.

(1) The carboxylic acid amide derivative of the above formula (I) wherein B is a 5- or 6-membered heterocyclic group which may be substituted by Y.

(2) The carboxylic acid amide derivative according to the above (1), wherein the heterocyclic group for B is one containing one or two atoms of at least one type selected from the group consisting of a nitrogen atom, a sulfur atom and an oxygen atom.

(3) The carboxylic acid amide derivative according to the above (1), wherein the heterocyclic group for B is pyridyl, thienyl or pyrazolyl.

(4) The carboxylic acid amide derivative of the above formula (I), wherein B is 3-trifluoromethyl-2-pyridyl, 3-methyl-2-thienyl or 1-methyl-3-trifluoromethyl-4-pyrazolyl.

(5) At least one carboxylic acid amide derivative of the above formula (I) selected from the group consisting N-[(3',4'-dichloro-1,1-dimethyl)phenacyl]-3-trifluoromethyl-2-pyridinecarboxamide (Compound No. 1), N-[(3',4'-dichloro-1,1-dimethyl)phenacyl]-3-methyl-2-thiophenecarboxamide (Compound No. 2), N-[(3',4'-dichloro-1,1-dimethyl)phenacyl]-1-methyl-3-trifluoromethyl-4-pyrazolecarboxamide (Compound No. 3), N-[[2'-methyl-4'-(2-propyloxy)-1,1-dimethyl]phenacyl]-3-trifluoromethyl-2-pyridinecarboxamide (Compound No. 4), N-[[2'-methyl-4'-(2-propyloxy)-1,1-dimethyl]phenacyl]-3-methyl-2-thiophenecarboxamide (Compound No. 5), N-[[2'-methyl-4'-(2-propyloxy)-1,1-dimethyl]phenacyl]-1-methyl-3-trifluoromethyl-4-pyrazolecarboxamide (Compound No. 6), N-[[4'-(2-propyloxy)-1,1-dimethyl]phenacyl]-3-trifluoromethyl-2-pyridinecarboxamide (Compound No. 7), N-[[4'-(2-propyloxy)-1,1-dimethyl]phenacyl]-3-methyl-2-thiophenecarboxamide (Compound No. 8), N-[[4'-(2-propyloxy)-1,1-dimethyl]phenacyl]-1-methyl-3-trifluoromethyl-4-pyrazolecarboxamide (Compound No. 9), N-[[2'-methyl-4'-(2-pentyloxy)-1,1-dimethyl]phenacyl]-3-trifluoromethyl-2-pyridinecarboxamide (Compound No. 10) and N-[[4'-(2-pentyloxy)-1,1-dimethyl]phenacyl]-3-trifluoromethyl-2-pyridinecarboxamide (Compound No. 11).

The fungicidal compound of the above (b) will be described. Among the fungicidal compounds, those having their common names already approved by ISO (International Organization for Standardization) will be represented by such common names. Other ones will be represented by chemical names, and those having their common names provisionally approved by ISO or having their common names applied to ISO for approval will be identified also by such common names.

An azole compound may, for example, be triadimefon, triflumizole, penconazole, flusilazole, myclobutanil, cyproconazole, tebuconazole, hexaconazole, N-propyl-N-[2-(2,4,6-trichlorophenoxy)ethyl]imidazole-1-carboxamide (prochloraz), metconazole, epoxiconazole, prothioconazole, triadimenol, difenoconazole, fluquinconazole, eniliconazol, imazalil, bitertanol, etaconazole, propiconazole, furconazole-cis, tetraconazole, oxpoconazole fumarate, flutriafol, fenbuconazole, bromuconazole, diniconazole, tricyclazole, probenazole, simeconazole, pent-4-enyl (2RS)-2-[furfuryl (imidazol-1-ylcarbonyl)amino]butyrate (pefurazoate), ipconazole, imibenconazole, cyazofamid, hymexazol, amisulbrom or fuberiazole. Among them, preferred is triflumizole, myclobutanil, cyproconazole, tebuconazole, hexaconazole, oxpoconazole fumarate, prochloraz, metconazole, epoxiconazole, prothioconazole, difenoconazole, tetraconazole, tricyclazole, cyazofamid or hymexazol.

An anilinopyrimidine compound may, for example, be mepanipyrim, pyrimethanil, cyprodinil or ferimzone.

A triazolopyrimidine compound may, for example, be 5-chloro-7-(4-methylpiperidin-1-yl)-6-(2,4,6-trifluorophenyl)-[1,2,4]triazolo[1,5-a]pyrimidine (Compound α).

A strobilurin compound may, for example, be azoxystrobin, kresoxim-methyl, metominostrobin, trifloxystrobin, picoxystrobin, (2E)-2-(methoxyimino)-2-[2-[(3E,5E,6E)-5-(methoxyimino)-4,6-dimethyl-2,8-dioxa-3,7-diazanona-3,6-dien-1-yl]phenyl]-N-methylacetamide (orysastrobin), dimoxystrobin, pyraclostrobin, fluoxastrobin or methyl 3-methoxy-2-[2-((((1-methyl-3-(4'-chlorophenyl)-2-propenylidene)amino)oxy)-methyl)phenyl]propenoate (enestrobin). Among them, preferred is azoxystrobin, kresoxim-methyl, trifloxystrobin, dimoxystrobin or pyraclostrobin.

An N-halogenothioalkyl compound may, for example, be captan, captafol or folpet. Among them, preferred is captan or folpet.

A pyridinamine compound may, for example, be fluazinam.

A bicarbonate may, for example, be sodium bicarbonate or potassium bicarbonate. Among them, potassium bicarbonate is preferred.

An inorganic sulfur compound may, for example, be sulfur, calcium polysulfide or zinc sulfate. Among them, sulfur is preferred.

A dithiocarbamate compound may, for example, be mancozeb, maneb, zineb, polycarbamate, metiram, propineb or thiram. Among them, mancozeb is preferred.

An organic chlorine compound may, for example, be chlorothalonil, fthalide or quintozene. Among them, chlorothalonil is preferred.

A dicarboxylmide compound may, for example, be procymidone, iprodione or vinclozolin. Among them, preferred is procymidone or iprodione.

An amine compound may, for example, be spiroxamine or dichlofluanid. Among them, spiroxamine is preferred.

A phenylpyrrole compound may, for example, be fludioxonil or fenpiclonil. Among them, fludioxonil is preferred.

A benzophenone compound may, for example, be metrafenone i.e. (3'-bromo-2,3,4,6'-tetramethoxy-2',6-dimethylbenzophenone).

A piperidine compound may, for example, be fenpropidin.

A dinitrobenzene compound may, for example, be meptyldinocap.

A morpholine compound may, for example, be fenpropimorph, tridemorph, dodemorph, dimethomorph or flumorph. Among them, preferred is dimethomorph or fenpropimorph.

A cyanoacetamide compound may, for example, be cymoxanil.

A phosphorous acid compound may, for example, be phosphorous acid, sodium phosphite, potassium phosphite or calcium phosphite. Among them, potassium phosphite is preferred.

An organophosphorus compound may, for example, be fosetyl-Al, tolclofos-methyl, S-benzyl O,O-diisopropylphosphorothioate, O-ethyl S,S-diphenylphosphorodithioate, aluminum ethyl hydrogenphosphonate, edifenphos or iprobenfos. Among them, preferred is fosetyl-Al or tolclofos-methyl.

A carboxamide compound may, for example, be flutolanil, 3,4-dichloro-2'-cyano-1,2-thiazole-5-carboxyanilide (isotianil), mepronil, zoxamid, tiadinil, carboxin, oxycarboxin, thifluzamide, furametpyr, penthiopyrad, boscalid, N-(3',4'-dichloro-5-fluorobiphenyl-2-yl)-3-(difluoromethyl)-1-methylpyrazole-4-carboxamide (bixafen), N-[2-[3-chloro-5-(trifluoromethyl)-2-pyridyl]ethyl]-α,α,α-trifluoro-o-toluamide (fluopyram), mixture of 2 syn-isomers 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 2 anti-isomers 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide (isopyrazam), silthiofam or fenhexamid. Among them, preferred is flutolanil or fenhexamid.

A quinoline compound may, for example, be quinoxyfen.

A copper compound may, for example, be copper oxychloride, cupric hydroxide, copper sulfate, bordeaux mixture or oxine copper. Among them, copper oxychloride is preferred.

A carbamate compound may, for example, be thiophanate-methyl, benomyl, carbendazim, thiabendazole, pyribencarb, diethofencarb, propamocarb hydrochloride, iprovalicarb, methyl[S—(R,S)]-3-[(N-isopropoxycarbonylvalinyl)amino]-3-(4-chlorophenyl)propionate (valiphenal) or benthiavalicarb-isopropyl. Among them, preferred is thiophanate-methyl, pyribencarb or propamocarb hydrochloride.

An antibiotic may, for example, be polyoxins, validamycin or kasugamycin. Among them, preferred is polyoxins or kasugamycin.

A guanidine compound may, for example, be iminoctadine or dodine. Among them, iminoctadine is preferred.

An oxime ether compound may, for example, be cyflufenamid.

4-Quinolinol derivatives may, for example, be Compound Nos. 1 to 11 disclosed on pages 8 to 14 in WO2001/92231. Among them, preferred is 2,3-dimethyl-6-t-butyl-8-fluoro-4-acetylquinoline (Compound β) disclosed as Compound 2 in the same publication.

Cyanomethylene compounds may, for example, be Compound Nos. 1 to 236 disclosed on pages 27 to 57 in WO2001/47902. Among them, preferred is 2-(2-fluoro-5-(trifluoromethyl)phenylthio)-2-(3-(2-methoxyphenyl)thiazolidin-2-yliden)acetonitrile (Compound γ) disclosed as Compound No. 120 in the same publication.

A quinazolinone compound may, for example, be proquinazid.

Benzoylpyridine compounds may, for example, be compounds disclosed in Tables 1 to 18 in WO2002/02527 and Tables 1 and 2 in WO2004/039155. Among them, preferred is 4-(2,3,4-trimethoxy-6-methylbenzoyl)-2,5-dichloro-3-trifluoromethylpyridine (Compound A), 4-(2,3,4-trimethoxy-6-methylbenzoyl)-2-chloro-3-trifluoromethyl-5-methoxypyridine (Compound B), 3-(2,3,4-trimethoxy-6-methylbenzoyl)-5-bromo-4-chloro-2-methoxypyridine (Compound C) or 3-(2,3,4-trimethoxy-6-methylbenzoyl)-5-chloro-2-methoxy-4-methylpyridine (Compound D).

Among the above-mentioned ones, (b) the fungicidal compound in the composition of the present invention is preferably at least one member selected from the group consisting of triflumizole, myclobutanil, cyproconazole, tebuconazole, hexaconazole, N-propyl-N-[2-(2,4,6-trichlorophenoxy)ethyl]imidazole-1-carboxamide (prochloraz), metconazole, epoxiconazole, prothioconazole, difenoconazole, tetraconazole, tricyclazole, oxpoconazole fumarate, cyazofamid, hymexazol, mepanipyrim, pyrimethanil, cyprodinil, ferimzone, 5-chloro-7-(4-methylpiperidin-1-yl)-6-(2,4,6-trifluorophenyl)-[1,2,4]triazolo[1,5-a]pyrimidine, azoxystrobin, kresoxim-methyl, trifloxystrobin, dimoxystrobin, pyraclostrobin, captan, folpet, fluazinam, potassium bicarbonate, sulfur, mancozeb, chlorothalonil, procymidone, iprodione, spiroxamine, fludioxonil, metrafenone, fenpropidin, meptyldinocap, dimethomorph, fenpropimorph, cymoxanil, potassium phosphite, fosetyl-Al, tolclofos-methyl, flutolanil, fenhexamid, quinoxyfen, copper oxychloride, thiophanate-methyl, pyribencarb, propamocarb hydrochloride, polyoxins, kasugamycin, iminoctadine, cyflufenamid, 2,3-dimethyl-6-t-butyl-8-fluoro-4-acetylquinoline, 2-(2-fluoro-5-(trifluoromethyl)phenylthio)-2-(3-(2-methoxyphenyl)thiazolidin-2-yliden)acetonitrile, proquinazid, 4-(2,3,4-trimethoxy-6-methylbenzoyl)-2,5-dichloro-3-trifluoromethylpyridine, 4-(2,3,4-trimethoxy-6-methylbenzoyl)-2-chloro-3-trifluoromethyl-5-methoxypyridine, 3-(2,3,4-trimethoxy-6-methylbenzoyl)-5-bromo-4-chloro-2-methoxypyridine and 3-(2,3,4-trimethoxy-6-methylbenzoyl)-5-chloro-2-methoxy-4-methylpyridine.

The composition of the present invention is useful as a fungicidal composition capable of controlling noxious fungi at a low dose, particularly useful as an agricultural or horticultural fungicidal composition. When used as an agricultural or horticultural fungicidal composition, the composition of the present invention is capable of controlling noxious fungi such as Oomycetes, Ascomycetes, Basidiomycetes, Deuteromycetes and particularly effective for controlling noxious fungi belonging to e.g. Ascomycetes or Deuteromycetes.

The following may be mentioned as specific examples of the above noxious fungi.

Oomycetes may, for example, be genus *Phytophthora*, such as potato or tomato late blight pathogen (*Phytophthora infestans*), or tomato haiiro-eki-byo pathogen (*Phytophthora capsici*); genus *Pseudoperonospora*, such as cucumber downy mildew pathogen (*Pseudoperonospora cubensis*); genus *Plasmopara*, such as grape downy mildew pathogen (*Plasmopara viticola*); and genus *Pythium*, such as rice seedling blight pathogen (*Pythium graminicola*), or wheat browning root rot pathogen (*Pythium iwayamai*).

Ascomycetes may, for example, be genus *Claviceps* such as false smut of rice (*Claviceps virens*); genus *Erysiphe*, such as wheat powdery mildew pathogen (*Erysiphe graminis*); genus *Sphaerotheca*, such as cucumber powdery mildew pathogen (*Sphaerotheca fuliginea*), or strawberry powdery mildew pathogen (*Sphaerotheca humuli*); genus *Uncinula*, such as grape powdery mildew pathogen (*Uncinula necator*); genus *Podosphaera*, such as apple powdery mildew pathogen (*Podosphaera leucotricha*); genus *Mycosphaerella*, such as garden pea *Mycosphaerella* blight pathogen (*Mycosphaerella pinodes*), apple fruit spot pathogen (*Mycosphaerella pomi*), banana black sigatoka pathogen (*Mycosphaerella musicola*), persimmons circular leaf spot pathogen (*Mycosphaerella nawae*), or strawberry leaf spot pathogen (*Mycosphaerella fragariae*); genus *Venturia*, such as apple scab pathogen (*Venturia inaequalis*), or pear scab pathogen (*Venturia nashicola*); genus *Pyrenophora*, such as barley net blotch pathogen (*Pyrenophora teres*), or barley stripe pathogen (*Pyrenophora graminea*); genus *Sclerotinia*, such as various *Sclerotinia* disease pathogen (*Sclerotinia Sclerotiorum*) such as kidney bean stem rot pathogen, cucumber *Sclerotinia* rot pathogen, cabbage *Sclerotinia* rot pathogen, Chinese cabbage *Sclerotinia* rot pathogen, red pepper *Sclerotinia* rot pathogen, sweet pepper *Sclerotinia* rot pathogen, onion watery soft rot pathogen, or rapeseed rot pathogen, wheat *Sclerotinia* snow blight pathogen (*Sclerotinia borealis*), tomato syoryu-kinkaku pathogen (*Sclerotinia minor*), or alfalfa *Sclerotinia* rot and crown rot pathogen (*Sclerotinia trifoliorum*); genus *Botryolinia*, such as peanut small *Sclerotinia* rot pathogen (*Botryolinia arachidis*); genus *Cochliobolus*, such as rice brown spot pathogen (*Cochliobolus miyabeanus*); genus *Didymella*, such as cucumber gummy stem blight pathogen (*Didymella bryoniae*); genus *Gibberella*, such as wheat *Fusarium* blight pathogen (*Gibberella zeae*); genus *Elsinoe*, such as grape anthracnose pathogen (*Elsinoe ampelina*), or citrus scab pathogen (*Elsinoe fawcettii*); genus *Diaporthe*, such as citrus melanose pathogen (*Diaporthe citri*), or grape swelling arm pathogen (*Diaporthe* sp.); genus *Guinardia*, such as grape black spot pathogen (*Guignardia bidwellii*); genus *Monilinia*, such as apple blossom blight pathogen (*Monilinia mali*), or peach brown rot pathogen (*Monilinia fructicola*); and genus *Glomerella*, such as grape ripe rot pathogen (*Glomerella cingulata*).

Basidiomycetes may, for example, be genus *Rhizoctonia*, such as rice sheath blight pathogen (*Rhizoctonia solani*); genus *Ustilago*, such as wheat loose smut pathogen (*Ustilago nuda*); genus *Puccinia*, such as oat crown rust pathogen (*Puccinia coronata*), wheat brown rust pathogen (*Puccinia recondita*), or wheat stripe rust pathogen (*Puccinia striiformis*); and genus *Typhula*, such as wheat or barley *Typhula* snow blight pathogen (*Typhula incarnata, Typhula ishikariensisis*).

Deuteromycetes may, for example, be genus *Septoria*, such as wheat glume blotch pathogen (*Septoria nodorum*), wheat speckled leaf blotch (*Septoria tritici*); genus *Botrytis*, such as various gray mold pathogen (*Botrytis cinerea*) such as grape gray mold pathogen, citrus gray mold pathogen, cucumber gray mold pathogen, tomato gray mold pathogen, strawberry gray mold pathogen, eggplant gray mold pathogen, kidney bean gray mold pathogen, adzuki bean gray mold pathogen, garden pea gray mold pathogen, peanut gray mold pathogen, red pepper gray mold pathogen, sweet pepper gray mold pathogen, lettuce gray mold pathogen, onion gray mold pathogen, statice gray mold pathogen, carnation gray mold pathogen, rose *Botrytis* blight pathogen, garden pansy gray mold pathogen, or sunflower gray mold pathogen, onion gray mold neck rot pathogen (*Botrytis allii*), or onion *Botrytis* hagare-syo (*Botrytis squamosa, Botrytis byssoidea, Botrytis tulipae*); genus *Pyricularia*, such as rice blast pathogen (*Pyricularia oryzae*); genus *Cercospora*, such as sugar beet *Cercospora* leaf spot pathogen (*Cercospora beticola*), or persimmons *Cercospora* leaf spot pathogen (*Cercospora kakivola*); genus *Colletotrichum*, such as cucumber anthracnose pathogen (*Colletotrichum orbiculare*); genus *Alternaria*, such as apple *Alternaria* leaf spot pathogen (*Alternaria alternata* apple pathotype), pear black spot pathogen (*Alternaria alternata* Japanese pear pathotype), potato or tomato early blight pathogen (*Alternaria solani*), cabbage or Chinese cabbage *Alternaria* leaf spot pathogen (*Alternaria brassicae*), cabbage *Alternaria* sooty spot pathogen (*Alternaria brassicola*), onion or Welsh onion *Alternaria* leaf spot pathogen (*Alternaria porri*), *Alternaria padwickii*; genus *Pseudocercosporella*, such as wheat eye spot pathogen (*Pseudocercosporella herpotrichoides*); genus *Pseudocercospora*, such as grape leaf spot pathogen (*Pseudocercospora vitis*); genus *Rhynchosporium*, such as barley scald pathogen (*Rhynchosporium secalis*); genus *Cladosporium*, such as peach scab pathogen (*Cladosporium carpophilum*); genus *Phomopsis*, such as peach *Phomopsis* rot pathogen (*Phomopsis* sp.); genus *Gloeosporium*, such as persimmons anthracnose pathogen (*Gloeosporium kaki*); genus *Fulvia*, such as tomato leaf mold pathogen (*Fulvia fulva*); genus *Corynespora*, such as cucumber *Corynespora* leaf spot pathogen (*Corynespora cassiicola*); genus *Curvularia*, such as *Curvularia intermedia, Curvularia clavata, Curvularia inaequalis, Curvularia ovoidea*; genus *Epicoccum* such as *Epicoccum purpurascens*.

The composition of the present invention is capable of controlling the above various noxious fungi and thus capable of preventively or curatively controlling various diseases. Particularly, the composition of the present invention is effective for controlling various diseases which are problematic in the agricultural and horticultural field, such as blast, brown spot, sheath blight or damping-off of rice (*Oryza sativa*, etc.); powdery mildew, scab, brown rust, stripe rust, net blotch, stripe, snow mold, snow blight, loose smut, eye spot, scald, leaf spot or glume blotch of cereals (*Hordeum vulgare, Tricum aestivum*, etc.); melanose or scab of citrus (*Citrus* spp., etc.); blossom blight, powdery mildew, melanose, *Alternaria* leaf spot or scab of apple (*Malus pumila*); scab or black spot of pear (*Pyrus serotina, Pyrus ussuriensis, Pyrus communis*); brown rot, scab or *Phomopsis* rot of peach (*Prunus persica*, etc.); anthracnose, ripe rot, leaf spot, swelling arm, powdery mildew or downy mildew of grape (*Vitis vinifera* spp., etc.); anthracnose, circular leaf spot or *Cercospora* leaf spot of Japanese persimmon (*Diospyros kaki*, etc.); anthracnose, powdery mildew, gummy stem blight, *corynespora* leaf spot or downy mildew of cucurbit (*Cucumis melo*, etc.); early blight, haiiro-eki-byo, leaf mold or late blight of tomato (*Lycopersicon esculentum*); black sigatoka of banana (*Musa sapientum*, etc.); *Cercospora* leaf spot of sugar beet (*Beta vulgaris* var. *saccharifera*, etc.); *Mycosphaerella* blight of garden pea (*Pisum sativum*); various *Alternaria* disease pathogens of cruciferous vegetables (*Brassica* sp., *Raphanus* sp., etc); late blight or early blight of potato (*Solanum tuberosum*); powdery mildew or leaf spot of strawberry (*Fragaria*, etc.); and gray mold or disease caused by *Sclerotinia* of various crops such as beans, vegetables, fruits or flowers. Among them, it is particularly effective against various gray mold or disease caused by *Sclerotinia* of cucumber (*Cucumis sativus*), kidney bean (*Phaseolus vulgaris*), adzuki bean (*Vigna angularis*), soybean (*Glycine max*), garden pea, peanut (*Arachis hypogaea*), tomato, strawberry, eggplant (*Solanum melongena*), red pepper (*Capsicum annuum*), sweet pepper (*Capsicum annuum*), lettuce (*Lactuca sativa*), onion (*Allium cepa*), grape, citrus, statice (*Limonium* spp.), carnation (*Dianthus* spp.), rose (*Rosa* spp.), garden pansy (*Viola*, etc.) or sunflower (*Helianthus annuus*).

Further, the composition of the present invention is effective also for preventive or curative control of soil diseases caused by plant pathogens such as *Fusarium, Pythium, Rhizoctonia, Verticillium* and *Plasmodiophora*.

Still further, the composition of the present invention is effective also to control various pathogens resistant to fungicides such as benzimidazoles, strobilurins, dicarboximides, phenylamides and ergosterol biosynthesis inhibitors.

Furthermore, the composition of the present invention has an excellent penetrative migration property, and when a pesticide containing the composition of the present invention is applied to soil, it is possible to control noxious fungi on stems and leaves at the same time as controlling noxious fungi in soil.

The composition of the present invention, is usually formulated by mixing above mentioned (a) the carboxylic acid amide derivative represented by the formula (I) or a salt thereof (hereinafter referred to simply as component (a)), and above mentioned (b) fungicidal compound (hereinafter referred to simply as component (b)), each of which may separately be mixed with various agricultural adjuvants in the same manner as conventional agricultural chemicals, and used in the form of a formulation such as a dust, granules, water-dispersible granules, a wettable powder, a water-based suspension concentrate, an oil-based suspension concentrate, water soluble granules, an emulsifiable concentrate, a soluble concentrate, a paste, an aerosol or an ultra low-volume formulation. However, so long as it is suitable for the purpose of the present invention, it may be formulated into any type of formulation which is commonly used in this field. Such agricultural adjuvants include solid carriers such as diatomaceous earth, slaked lime, calcium carbonate, talc, white carbon, kaoline, bentonite, kaolinite, sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethylsulfoxide, N,N-dimethylformamide, dimethylacetamide, N-methyl-2-pyrrolidone, and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Such adjuvants may be selected for use among these known in this field, so long as such selection does not depart from the purpose of the present invention. Further, it is possible to use commonly employed various additives such as a filler, a thickener, an anti-settling agent, an anti-freezing agent, a dispersion stabilizer, a phytotoxicity reducing agent, an anti-mold agent, etc. The blend ratio of the components (a) and (b) as active components to various additives is usually from 0.005:99.995 to 95:5, preferably from 0.2:99.8 to 90:10. In actual use of such a formulation, it may be used as it is, or it may be diluted with a diluting agent such as water to a predetermined concentration, and as a case requires, various extenders may be added.

In the composition of the present invention, a proper blend weight ratio of component (a) to component (b) varies by a difference in weather conditions, crop plants concerned, the method of use, the formulation, etc., and can not simply be defined, but it is usually from 1:70,000 to 70,000:1, preferably from 1:1,000 to 70,000:1. Further, a more preferred blend weight ratio of component (a) to component (b) may be mentioned with respect to each fungicidal compound of component (b). Namely, for example, in a case where component (b) is an azole compound, it is from 1:100 to 70,000:1; in a case where component (b) is an anilinopyrimidine compound, it is from 1:100 to 500:1; in a case where component (b) is at least one fungicidal compound selected from the group consisting of an N-halogenothioalkyl compound, a pyridinamine compound, a bicarbonate, an inorganic sulfur compound, a dithiocarbamate compound, a dicarboxylmide compound, a morpholine compound, a cyanoacetamide compound, a phosphorous acid compound, a carboxamide compound and an antibiotic, it is from 1:500 to 200:1; in a case where component (b) is a copper compound and/or a carbamate compound, it is from 1:1,000 to 200:1; in a case where component (b) is a benzophenone compound, it is from 1:100 to 40,000:1; in a case where component (b) is a quinoline compound and/or a benzoylpyridine compound, it is from 1:100 to 5,000:1; and in the case of other compounds, it is from 1:100 to 200:1.

The composition of the present invention may be applied by an application method which is commonly used, such as spreading (spreading, spraying, misting, atomizing, grain diffusing or application on water surface), soil application (such as mixing or irrigation) or surface application (such as coating, dust coating or covering). Further, it may be applied also by so-called ultra low volume. In this method, the formulation may contain 100% of the active ingredient. In its application, it is possible to optionally select an application to noxious fungi or to a site where they grow (the application may be pre-emergence or post-emergence of such noxious fungi). Further, the components (a) and (b) may be separately formulated, and at the time of application, they may be mixed and applied. Otherwise, they may be formulated together and applied. The formulation may be applied as it is or after being diluted with e.g. water.

The dose of the composition of the present invention varies depending upon the weather conditions, crop plants, method of use, formulation, etc. and can not be generally defined. However, in the case of foliage treatment, it is applied so that the total amount of components (a) and (b) as active ingredients will be at a concentration of usually from 0.1 to 10,000 ppm, preferably from 1 to 4,000 ppm, more preferably from 1 to 2,000 ppm, and in the case of soil treatment, it is applied so that the total amount of components (a) and (b) as active ingredients will be usually from 10 to 100,000 g/ha, preferably from 200 to 20,000 g/ha.

Additionally, the composition of the present invention may be mixed with or may be used in combination with other agricultural chemicals, fertilizers or phytotoxicity-reducing agents, whereby synergistic effects or activities may sometimes be obtained. Such other agricultural chemicals may, for example, be a fungicide, an insecticide, a miticide, a nematicide, a herbicide, an antivirus agent, an attractant, a plant hormone and a plant growth regulating agent.

The active ingredient compounds (common names; including some which are under application, or test code of the Japan Plant Protection Association) of the fungicides in such other agricultural chemicals, may, for example, be:

a phenylamide compound such as metalaxyl, metalaxyl-M, mefenoxam, oxadixyl, ofurace, benalaxyl, benalaxyl-M (another name: kiralaxyl or chiralaxyl), furalaxyl or cyprofuram;
  a piperazine compound such as triforine;
  a pyridine compound such as pyrifenox;
  a carbinol compound such as fenarimol or flutriafol;
  an oxazolidinone compound such as famoxadone;
  a thiazole carboxamide compound such as ethaboxam;
  an imidazolidine compound such as fenamidone
  a benzenesulfoneamide compound such as flusulfamid;
  an oxime ether compound such as cyflufenamid;
  a phenoxy amide compound such as fenoxanil;
  an anthraquinone compound;
  a crotonic acid compound;
  an azole compound such as triadimefon, triflumizole, penconazole, flusilazole, myclobutanil, cyproconazole, tebuconazole, hexaconazole, N-propyl-N-[2-(2,4,6-trichlorophenoxy)ethyl]imidazole-1-carboxamide (prochloraz), metconazole, epoxiconazole, prothioconazole, triadimenol, difenoconazole, fluquinconazole, eniliconazol, imazalil, bitertanol, etaconazole, propiconazole, furconazole-cis, tetraconazole, oxpoconazole fumarate, flutriafol, fenbuconazole, bromuconazole, diniconazole, tricyclazole, probenazole, simeconazole, pent-4-enyl (2RS)-2-[furfuryl(imidazol-1-yl-carbonyl)amino]butyrate (pefurazoate), ipconazole, imibenconazole, cyazofamid, hymexazol, amisulbrom or fuberiazole;
  an anilinopyrimidine compound such as mepanipyrim, pyrimethanil, cyprodinil or ferimzone;
  a triazolopyrimidine compound such as 5-chloro-7-(4-methylpiperidin-1-yl)-6-(2,4,6-trifluorophenyl)-[1,2,4]triazolo [1,5-a]pyrimidine;
  a strobilurin compound such as azoxystrobin, kresoxim-methyl, metominostrobin, trifloxystrobin, picoxystrobin, (2E)-2-(methoxyimino)-2-[2-[(3E,5E,6E)-5-(methoxyimino)-4,6-dimethyl-2,8-dioxa-3,7-diazanona-3,6-dien-1-yl]phenyl]-N-methylacetamide (orysastrobin), dimoxystrobin, pyraclostrobin, fluoxastrobin, or methyl 3-methoxy-2-[2-((((1-methyl-3-(4'-chlorophenyl)-2-propenylidene)amino)oxy)-methyl)phenyl]propenoate (enestrobin);
  an N-halogenothioalkyl compound such as captan, captafol or folpet;
  a pyridinamine compound such as fluazinam;
  a bicarbonate such as sodium bicarbonate or potassium bicarbonate;
  an inorganic sulfur compound such as sulfur, calcium polysulfide or zinc sulfate;
  a dithiocarbamate compound such as mancozeb, maneb, zineb, polycarbamate, metiram, propineb or thiram;
  an organic chlorine compound such as chlorothalonil, fthalide or quintozene;
  a dicarboxylmide compound such as procymidone, iprodione or vinclozolin;
  an amine compound such as spiroxamine or dichlofluanid;
  a phenylpyrrole compound such as fludioxonil or fenpiclonil;
  a benzophenone compound such as metrafenone (3'-bromo-2,3,4,6'-tetramethoxy-2',6-dimethylbenzophenone);
  a dinitrobenzene compound such as meptyldinocap;
  a piperidine compound such as fenpropidin;
  a morpholine compound such as fenpropimorph, tridemorph, dodemorph, dimethomorph or flumorph;
  a cyanoacetamide compound such as cymoxanil;
  a phosphorous acid compound such as phosphorus acid, sodium primary phosphite, potassium primary phosphite, calcium primary phosphite, sodium secondary phosphite, potassium secondary phosphite or calcium secondary phosphite;
  an organophosphorus compound such as fosetyl-Al, tolcofos-methyl, S-benzyl O,O-diisopropyl phosphorothioate, O-ethyl S,S-diphenyl phosphorodithioate, aluminum ethyl hydrogenphosphonate, edifenphos or iprobenfos;
  a carboxamide compound such as flutolanil, 3,4-dichloro-2'-cyano-1,2-thiazole-5-carboxyanilide (isotianil), mepronil, zoxamid, tiadinil, carboxin, oxycarboxin, thifluzamide, furametpyr, penthiopyrad, boscalid, N-(3',4'-dichloro-5-fluorobiphenyl-2-yl)-3-(difluoromethyl)-1-methylpyrazole-4-carboxamide (bixafen), N-[2-[3-chloro-5-(trifluoromethyl)-2-pyridyl]ethyl]-α,α,α-trifluoro-o-toluamide (fluopyram), mixture of 2 syn-isomers 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 2 anti-isomers 3-(difluoromethyl)-1-methyl-N-[(1RS,4SR,9SR)-1,2,3,4-tetrahydro-9-isopropyl-1,4-methanonaphthalen-5-yl] pyrazole-4-carboxamide (isopyrazam), silthiofam or fenhexamid;
  a quinoline compound such as quinoxyfen;
  a copper compound such as copper oxychloride, cupric hydroxide, copper sulfate, bordeaux mixture or oxine copper;

a carbamate compound such as thiophanate-methyl, benomyl, carbendazim, thiabendazole, pyribencarb, diethofencarb, propamocarb hydrochloride, iprovalicarb, methyl[S—(R,S)]-3-[(N-isopropoxycarbonylvalinyl)-amino]-3-(4-chlorophenyl)propanoate (valiphenal) or benthiavalicarb-isopropyl;

an antibiotic such as polyoxins, validamycin or kasugamycin;

a guanidine compound such as iminoctadine or dodine;

a 4-quinolinol derivative compound such as 2,3-dimethyl-6-t-butyl-8-fluoro-4-acetylquinoline;

a cyanomethylene compound such as 2-(2-fluoro-5-(trifluoromethyl)phenylthio)-2-(3-(2-methoxyphenyl)thiazolidin-2-ylidene)acetonitrile;

a benzoylpyridine compound such as 4-(2,3,4-trimethoxy-6-methylbenzoyl)-2,5-dichloro-3-trifluoromethylpyridine, 4-(2,3,4-trimethoxy-6-methylbenzoyl)-2-chloro-3-trifluoromethyl-5-methoxypyridine, 3-(2,3,4-trimethoxy-6-methylbenzoyl)-5-bromo-4-chloro-2-methoxypyridine or 3-(2,3,4-trimethoxy-6-methylbenzoyl)-5-chloro-2-methoxy-4-methylpyridine; or other compounds, such as proquinazid, isoprothiolane, pyroquilon, diclomezine, chloropicrin, dazomet, metam-sodium, UBF-307, diclocymet, Syngenta 446510 (mandipropamid, dipromandamid), fluopicolide, carpropamid, BCF051, BCM061 and BCM062.

Now, among the above fungicidal compositions of the present invention, some of preferred combinations not described above will be exemplified.

(1) A fungicidal composition comprising synergistically effective amounts of (a) the carboxylic acid amide derivative of the above formula (I) or its salt, and (b) at least one fungicidal compound selected from the group consisting of an azole compound, an anilinopyrimidine compound, a strobilurin compound, an N-halogenothioalkyl compound, a pyridinamine compound, a dithiocarbamate compound, an organic chlorine compound, a dicarboxylmide compound, an amine compound, a phenylpyrrole compound, a benzophenone compound, a piperidine compound, a morpholine compound, a cyanoacetamide compound, an organophosphorus compound, a carboxamide compound, a quinoline compound, a copper compound, a carbamate compound, an antibiotic, a guanidine compound and a benzoylpyridine compound.

(2) The composition according to the above (1), wherein (b) the fungicidal compound is at least one member selected from the group consisting of triadimefon, triflumizole, penconazole, flusilazole, myclobutanil, cyproconazole, tebuconazole, hexaconazole, N-propyl-N-[2-(2,4,6-trichlorophenoxy)ethyl]imidazole-1-carboxamide, metconazole, epoxiconazole, prothioconazole, triadimenol, difenoconazole, fluquinconazole, eniliconazol, imazalil, bitertanol, etaconazole, propiconazole, furconazole-cis, tetraconazole, oxpoconazole fumarate, flutriafol, fenbuconazole, bromuconazole, diniconazole, tricyclazole, probenazole, simeconazole, pent-4-enyl (2RS)-2-[furfuryl(imidazol-1-ylcarbonyl)amino]butyrate, ipconazole, imibenconazole, cyazofamid, hymexazol, amisulbrom, fuberiazole, mepanipyrim, pyrimethanil, cyprodinil, azoxystrobin, kresoxim-methyl, metominostrobin, trifloxystrobin, picoxystrobin, (2E)-2-(methoxyimino)-2-[2-[(3E,5E,6E)-5-(methoxyimino)-4,6-dimethyl-2,8-dioxa-3,7-diazanona-3,6-dien-1-yl]phenyl]-N-methylacetamide, dimoxystrobin, pyraclostrobin, fluoxastrobin, methyl 3-methoxy-2-[2-((((1-methyl-3-(4'-chlorophenyl)-2-propenylidene)amino)oxy)-methyl)phenyl]propenoate, captan, captafol, folpet, fluazinam, mancozeb, maneb, zineb, polycarbamate, metiram, propineb, thiram, chlorothalonil, fthalide, quintozene, procymidone, iprodione, vinclozolin, spiroxamine, dichlofluanid, fludioxonil, fenpiclonil, metrafenone, fenpropidin, fenpropimorph, tridemorph, dodemorph, dimethomorph, flumorph, cymoxanil, tolclofos-methyl, S-benzyl O,O-diisopropylphosphorothioate, O-ethyl S,S-diphenylphosphorodithioate, aluminum ethyl hydrogenphosphonate, edifenphos, iprobenfos, flutolanil, 3,4-dichloro-2'-cyano-1,2-thiazole-5-carboxyanilide, mepronil, zoxamid, tiadinil, carboxin, oxycarboxin, thifluzamide, furametpyr, penthiopyrad, boscalid, N-(3',4'-dichloro-5-fluorobiphenyl-2-yl)-3-(difluoromethyl)-1-methylpyrazole-4-carboxamide, N-[2-[3-chloro-5-(trifluoromethyl)-2-pyridyl]ethyl]-α,α,α-trifluoro-o-toluamide, mixture of 2 syn-isomers 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 2 anti-isomers 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide, silthiofam, fenhexamid, quinoxyfen, copper oxychloride, cupric hydroxide, copper sulfate, bordeaux mixture, oxine copper, thiophanate-methyl, benomyl, carbendazim, thiabendazole, pyribencarb, diethofencarb, propamocarb hydrochloride, iprovalicarb, methyl[S—(R,S)]-3-[(N-isopropoxycarbonylvalinyl)-amino]-3-(4-chloro-phenyl)propanoate, benthiavalicarb-isopropyl, polyoxins, validamycin, kasugamycin, iminoctadine, dodine, 4-(2,3,4-trimethoxy-6-methylbenzoyl)-2,5-dichloro-3-trifluoromethylpyridine, 4-(2,3,4-trimethoxy-6-methylbenzoyl)-2-chloro-3-trifluoromethyl-5-methoxypyridine, 3-(2,3,4-trimethoxy-6-methylbenzoyl)-5-bromo-4-chloro-2-methoxypyridine and 3-(2,3,4-trimethoxy-6-methylbenzoyl)-5-chloro-2-methoxy-4-methylpyridine.

(3) The composition according to the above (2), wherein (b) the fungicidal compound is at least one member selected from the group consisting of cyproconazole, tebuconazole, N-propyl-N-[2-(2,4,6-trichlorophenoxy)ethyl]imidazole-1-carboxamide, metconazole, epoxiconazole, prothioconazole, difenoconazole, tetraconazole, oxpoconazole fumarate, cyazofamid, mepanipyrim, pyrimethanil, cyprodinil, azoxystrobin, kresoxim-methyl, trifloxystrobin, pyraclostrobin, captan, folpet, fluazinam, mancozeb, chlorothalonil, procymidone, iprodione, spiroxamine, fludioxonil, metrafenone, fenpropidin, fenpropimorph, cymoxanil, fosetyl-Al, flutolanil, fenhexamid, quinoxyfen, copper oxychloride, thiophanate-methyl, pyribencarb, polyoxins, iminoctadine, 4-(2,3,4-trimethoxy-6-methylbenzoyl)-2,5-dichloro-3-trifluoromethylpyridine, 4-(2,3,4-trimethoxy-6-methylbenzoyl)-2-chloro-3-trifluoromethyl-5-methoxypyridine, 3-(2,3,4-trimethoxy-6-methylbenzoyl)-5-bromo-4-chloro-2-methoxypyridine and 3-(2,3,4-trimethoxy-6-methylbenzoyl)-5-chloro-2-methoxy-4-methylpyridine.

Now, Test Examples of the present invention will be described, but it should be understood that the present invention is by no means thereby restricted. Compound No. in each Test Example corresponds to Compound No. shown in the above exemplification of the carboxylic acid amide derivative of the formula (I).

TEST EXAMPLE 1

Test on Preventive Effect Against Wheat Powdery Mildew

Wheat (cultivar: Norin-61-go) was cultivated in a plastic pot having a diameter of 7.5 cm, and when it reached 1.5-leaf stage, a mixed chemical solution having the respective test compounds adjusted to prescribed concentrations, was applied by a spray gun in an amount of 10 ml per seedling.

After the chemical solution dried, conidia of *Erysiphe graminis* were dusted and inoculated and maintained in a constant temperature chamber at 20° C. From 7 to 8 days after the inoculation, the area of sporulation was investigated, and the diseased area ratio to non-treated section was obtained by the following equation. The results are shown in Tables 1-1 to 1-101.

Diseased area ratio to non-treated section=$(a/b) \times 100$ a: Average area of sporulation in treated section b: Average area of sporulation in non-treated section Further, the theoretical value was calculated by a Colby's formula and shown in brackets ( ) in Tables 1-1 to 1-101. Since the diseased area ratio to non-treated section (experimental value) is lower than the theoretical value, the composition of the present invention can be said to have a synergistic effect.

TABLE 1-1

| Concentration of cyproconazole | Concentration of Compound No. 4 (ppm) | | | |
|---|---|---|---|---|
| (ppm) | 63 | 31 | 16 | 0 |
| 0.5 | 0 (0.9) | 0 (1.2) | 0 (4.5) | 60.0 |
| 0.125 | 0 (1.5) | 0 (2.0) | 0 (7.3) | 97.5 |
| 0 | 1.5 | 2.0 | 7.5 | — |

TABLE 1-2

| Concentration of cyproconazole | Concentration of Compound No. 5 (ppm) | | | |
|---|---|---|---|---|
| (ppm) | 63 | 31 | 16 | 0 |
| 0.5 | 0 (0.9) | 0 (1.5) | 0 (9.0) | 60.0 |
| 0.25 | 0 (1.2) | 0 (2.0) | 0 (12.0) | 80.0 |
| 0.125 | 0 (1.5) | 0 (2.4) | 0 (14.6) | 97.5 |
| 0 | 1.5 | 2.5 | 15.0 | — |

TABLE 1-3

| Concentration of cyproconazole | Concentration of Compound No. 8 (ppm) | | |
|---|---|---|---|
| (ppm) | 125 | 63 | 0 |
| 0.5 | 0 (9.0) | 0 (10.5) | 60.0 |
| 0.25 | 0 (12.0) | 0 (14.0) | 80.0 |
| 0.125 | 0 (14.6) | 0 (17.1) | 97.5 |
| 0 | 15.0 | 17.5 | — |

TABLE 1-4

| Concentration of cyproconazole | Concentration of Compound No. 11 (ppm) | | |
|---|---|---|---|
| (ppm) | 250 | 63 | 0 |
| 0.5 | 0 (21.0) | 3.0 (51.0) | 60.0 |
| 0.25 | 0 (28.0) | 5.0 (68.0) | 80.0 |
| 0 | 35.0 | 85.0 | — |

TABLE 1-5

| Concentration of tebuconazole (ppm) | Concentration of Compound No. 4 (ppm) | | |
|---|---|---|---|
|  | 125 | 31 | 0 |
| 1 | 0 (0.25) | 0 (0.38) | 5.0 |
| 0.25 | 0 (2.0) | 0 (3.0) | 40.0 |
| 0 | 5.0 | 7.5 | — |

TABLE 1-6

| Concentration of tebuconazole (ppm) | Concentration of Compound No. 5 (ppm) | | |
|---|---|---|---|
|  | 125 | 63 | 0 |
| 1 | 0 (0.13) | 0 (0.13) | 5.0 |
| 0.5 | 0 (0.25) | 0 (0.25) | 10.0 |
| 0.25 | 0 (1.0) | 0 (1.0) | 40.0 |
| 0 | 2.5 | 2.5 | — |

TABLE 1-7

| Concentration of tebuconazole (ppm) | Concentration of Compound No. 8 (ppm) | | | |
|---|---|---|---|---|
|  | 250 | 125 | 63 | 0 |
| 1 | 0 (0.5) | 0 (1.5) | 2.0 (3.0) | 5.0 |
| 0.5 | 0 (1.0) | 0 (3.0) | 2.0 (6.0) | 10.0 |
| 0 | 10.0 | 30.0 | 60.0 | — |

TABLE 1-8

| Concentration of tebuconazole (ppm) | Concentration of Compound No. 11 (ppm) | | | |
|---|---|---|---|---|
|  | 250 | 125 | 63 | 0 |
| 1 | 0 (0.63) | 0 (1.3) | 0 (3.0) | 5.0 |
| 0.5 | 0 (1.3) | 0 (2.5) | 2.0 (6.0) | 10.0 |
| 0.25 | 0 (5.0) | 2.0 (10.0) | 5.0 (24.0) | 40.0 |
| 0 | 12.5 | 25.0 | 60.0 | — |

TABLE 1-9

| Concentration of epoxiconazole (ppm) | Concentration of Compound No. 4 (ppm) | | | |
|---|---|---|---|---|
|  | 250 | 125 | 63 | 0 |
| 1 | 0 (0.02) | 0 (0.11) | 0 (0.24) | 3.0 |
| 0.5 | 0 (0.13) | 0 (0.76) | 0 (1.7) | 21.2 |
| 0.25 | 0 (0.36) | 0 (2.2) | 0 (4.8) | 60.6 |
| 0 | 0.6 | 3.6 | 7.9 | — |

TABLE 1-10

| Concentration of epoxiconazole (ppm) | Concentration of Compound No. 5 (ppm) | | | |
|---|---|---|---|---|
|  | 250 | 125 | 63 | 0 |
| 1 | 0 (0.02) | 0 (0.02) | 0 (0.11) | 3.0 |
| 0.5 | 0 (0.13) | 0 (0.13) | 0 (0.76) | 21.2 |
| 0 | 0.6 | 0.6 | 3.6 | — |

TABLE 1-11

| Concentration of epoxiconazole (ppm) | Concentration of Compound No. 8 (ppm) | | |
|---|---|---|---|
| | 250 | 63 | 0 |
| 0.5 | 0 (1.9) | 3.6 (4.5) | 21.2 |
| 0.25 | 0 (5.5) | 6.1 (12.8) | 60.6 |
| 0 | 9.1 | 21.2 | — |

TABLE 1-12

| Concentration of epoxiconazole (ppm) | Concentration of Compound No. 11 (ppm) | | | |
|---|---|---|---|---|
| | 250 | 125 | 63 | 0 |
| 1 | 0 (0.46) | 0 (0.64) | 0 (0.73) | 3.0 |
| 0.5 | 0 (3.2) | 0 (4.5) | 0 (5.1) | 21.2 |
| 0.25 | 0 (9.2) | 3.6 (12.8) | 3.6 (14.7) | 60.6 |
| 0 | 15.2 | 21.2 | 24.2 | — |

TABLE 1-13

| Concentration of tetraconazole (ppm) | Concentration of Compound No. 4 (ppm) | | | |
|---|---|---|---|---|
| | 63 | 31 | 16 | 0 |
| 0.5 | 0 (0.79) | 0 (1.1) | 0 (3.9) | 52.5 |
| 0.25 | 0 (0.86) | 0 (1.2) | 0 (4.3) | 57.5 |
| 0.125 | 0 (0.90) | 0 (1.2) | 2.0 (4.5) | 60.0 |
| 0 | 1.5 | 2.0 | 7.5 | — |

TABLE 1-14

| Concentration of tetraconazole (ppm) | Concentration of Compound No. 5 (ppm) | | | |
|---|---|---|---|---|
| | 63 | 31 | 16 | 0 |
| 0.25 | 0 (0.86) | 0 (1.4) | 0 (8.6) | 57.5 |
| 0.125 | 0 (0.90) | 0 (1.5) | 0 (9.0) | 60.0 |
| 0 | 1.5 | 2.5 | 15.0 | — |

TABLE 1-15

| Concentration of tetraconazole (ppm) | Concentration of Compound No. 8 (ppm) | | | |
|---|---|---|---|---|
| | 250 | 125 | 63 | 0 |
| 0.5 | 0 (6.6) | 0 (7.9) | 0 (9.2) | 52.5 |
| 0.125 | 1.0 (7.5) | 1.0 (9.0) | 5.0 (10.5) | 60.0 |
| 0 | 12.5 | 15.0 | 17.5 | — |

TABLE 1-16

| Concentration of tetraconazole (ppm) | Concentration of Compound No. 11 (ppm) | | | |
|---|---|---|---|---|
| | 250 | 125 | 63 | 0 |
| 0.5 | 2.0 (18.4) | 10.0 (31.5) | 20.0 (44.6) | 52.5 |
| 0.25 | 3.0 (20.1) | 20.0 (34.5) | 30.0 (48.9) | 57.5 |
| 0.125 | 5.0 (21.0) | 25.0 (36.0) | 30.0 (51.0) | 60.0 |
| 0 | 35.0 | 60.0 | 85.0 | — |

TABLE 1-17

| Concentration of cyprodinil (ppm) | Concentration of Compound No. 4 (ppm) | | | |
|---|---|---|---|---|
| | 63 | 31 | 16 | 0 |
| 125 | 0 (0.33) | 0 (2.1) | 0 (4.1) | 32.5 |
| 63 | 0 (0.70) | 0 (4.6) | 0 (8.8) | 70.0 |
| 31 | 0 (0.75) | 0 (4.9) | 2.0 (9.4) | 75.0 |
| 0 | 1.0 | 6.5 | 12.5 | — |

TABLE 1-18

| Concentration of cyprodinil (ppm) | Concentration of Compound No. 5 (ppm) | | | |
|---|---|---|---|---|
| | 63 | 31 | 16 | 0 |
| 125 | 0 (0.16) | 0 (0.81) | 0 (2.6) | 32.5 |
| 63 | 0 (0.35) | 0 (1.8) | 0 (5.6) | 70.0 |
| 31 | 0 (0.38) | 0 (1.9) | 0 (6.0) | 75.0 |
| 0 | 0.5 | 2.5 | 8.0 | — |

TABLE 1-19

| Concentration of cyprodinil (ppm) | Concentration of Compound No. 7 (ppm) | | | |
|---|---|---|---|---|
| | 31 | 16 | 8 | 0 |
| 125 | 0 (1.3) | 0 (8.1) | 5.0 (9.8) | 32.5 |
| 63 | 0 (2.8) | 0 (17.5) | 8.0 (21.0) | 70.0 |
| 31 | 0 (3.0) | 5.0 (18.8) | 10.0 (22.5) | 75.0 |
| 0 | 4.0 | 25.0 | 30.0 | — |

TABLE 1-20

| Concentration of cyprodinil (ppm) | Concentration of Compound No. 11 (ppm) | | | |
|---|---|---|---|---|
| | 250 | 125 | 63 | 0 |
| 125 | 0 (5.7) | 5.0 (19.5) | 15.0 (22.8) | 32.5 |
| 63 | 0 (12.3) | 5.0 (42.0) | 25.0 (49.0) | 70.0 |
| 31 | 0 (13.1) | 15.0 (45.0) | 30.0 (52.5) | 75.0 |
| 0 | 17.5 | 60.0 | 70.0 | — |

TABLE 1-21

| Concentration of kresoxim-methyl (ppm) | Concentration of Compound No. 4 (ppm) | | | |
|---|---|---|---|---|
| | 250 | 125 | 63 | 0 |
| 25 | 0 (0.01) | 0 (0.06) | 0 (0.14) | 1.8 |
| 12.5 | 0 (0.03) | 0 (0.18) | 0 (0.39) | 4.9 |
| 0 | 0.6 | 3.6 | 7.9 | — |

TABLE 1-22

| Concentration of kresoxim-methyl (ppm) | Concentration of Compound No. 5 (ppm) | | | |
|---|---|---|---|---|
| | 250 | 125 | 63 | 0 |
| 25 | 0 (0.01) | 0 (0.01) | 0 (0.06) | 1.8 |
| 12.5 | 0 (0.03) | 0 (0.03) | 0 (0.18) | 4.9 |
| 0 | 0.6 | 0.6 | 3.6 | — |

TABLE 1-23

| Concentration of kresoxim- | Concentration of Compound No. 8 (ppm) | | | |
|---|---|---|---|---|
| methyl (ppm) | 250 | 125 | 63 | 0 |
| 25 | 0 (0.16) | 0 (0.27) | 0 (0.38) | 1.8 |
| 12.5 | 0 (0.45) | 0 (0.74) | 0 (1.0) | 4.9 |
| 6.3 | 0 (0.56) | 0 (0.93) | 0 (1.3) | 6.1 |
| 0 | 9.1 | 15.2 | 21.2 | — |

TABLE 1-24

| Concentration of kresoxim- | Concentration of Compound No. 11 (ppm) | | | |
|---|---|---|---|---|
| methyl (ppm) | 250 | 125 | 63 | 0 |
| 25 | 0 (0.03) | 0 (0.03) | 0 (0.03) | 1.8 |
| 12.5 | 0 (0.09) | 0 (0.09) | 0 (0.09) | 4.9 |
| 6.3 | 0 (0.11) | 0 (0.11) | 0 (0.11) | 6.1 |
| 0 | 1.8 | 1.8 | 1.8 | — |

TABLE 1-25

| Concentration of spiroxamine | Concentration of Compound No. 4 (ppm) | | | |
|---|---|---|---|---|
| (ppm) | 250 | 125 | 63 | 0 |
| 50 | 0 (0.04) | 0 (0.22) | 0 (0.48) | 6.1 |
| 12.5 | 0 (0.58) | 0 (3.5) | 0 (7.7) | 97.0 |
| 0 | 0.6 | 3.6 | 7.9 | — |

TABLE 1-26

| Concentration of spiroxamine | Concentration of Compound No. 5 (ppm) | | | |
|---|---|---|---|---|
| (ppm) | 250 | 125 | 63 | 0 |
| 50 | 0 (0.04) | 0 (0.04) | 0 (0.22) | 6.1 |
| 25 | 0 (0.09) | 0 (0.09) | 0 (0.55) | 15.2 |
| 0 | 0.6 | 0.6 | 3.6 | — |

TABLE 1-27

| Concentration of spiroxamine | Concentration of Compound No. 8 (ppm) | | | |
|---|---|---|---|---|
| (ppm) | 250 | 125 | 63 | 0 |
| 50 | 0 (0.56) | 0 (0.93) | 0 (1.3) | 6.1 |
| 25 | 0 (1.4) | 0 (2.3) | 0 (3.2) | 15.2 |
| 12.5 | 0 (8.8) | 0 (14.7) | 6.1 (20.6) | 97.0 |
| 0 | 9.1 | 15.2 | 21.2 | — |

TABLE 1-28

| Concentration of spiroxamine | Concentration of Compound No. 11 (ppm) | | | |
|---|---|---|---|---|
| (ppm) | 250 | 125 | 63 | 0 |
| 50 | 0 (0.93) | 0 (1.3) | 1.2 (1.5) | 6.1 |
| 12.5 | 6.1 (14.7) | 14.6 (20.6) | 12.1 (23.5) | 97.0 |
| 0 | 15.2 | 21.2 | 24.2 | — |

TABLE 1-29

| Concentration of fludioxonil | Concentration of Compound No. 4 (ppm) | | | |
|---|---|---|---|---|
| (ppm) | 63 | 31 | 16 | 0 |
| 500 | 0 (0.85) | 0 (5.5) | 0 (10.6) | 85.0 |
| 250 | 0 (0.90) | 0 (5.9) | 3.0 (11.3) | 90.0 |
| 125 | 0 (0.95) | 0 (6.2) | 5.0 (11.9) | 95.0 |
| 0 | 1.0 | 6.5 | 12.5 | — |

TABLE 1-30

| Concentration of fludioxonil | Concentration of Compound No. 5 (ppm) | | | |
|---|---|---|---|---|
| (ppm) | 63 | 31 | 16 | 0 |
| 500 | 0 (0.43) | 0 (2.1) | 0 (6.8) | 85.0 |
| 250 | 0 (0.45) | 0 (2.3) | 0 (7.2) | 90.0 |
| 125 | 0 (0.48) | 0 (2.4) | 3.0 (7.6) | 95.0 |
| 0 | 0.5 | 2.5 | 8.0 | — |

TABLE 1-31

| Concentration of fludioxonil | Concentration of Compound No. 7 (ppm) | | | |
|---|---|---|---|---|
| (ppm) | 31 | 16 | 8 | 0 |
| 500 | 0 (3.4) | 5.0 (21.3) | 15.0 (25.5) | 85.0 |
| 250 | 0 (3.6) | 15.0 (22.5) | 20.0 (27.0) | 90.0 |
| 125 | 0 (3.8) | 15.0 (23.8) | 20.0 (28.5) | 95.0 |
| 0 | 4.0 | 25.0 | 30.0 | — |

TABLE 1-32

| Concentration of fludioxonil | Concentration of Compound No. 11 (ppm) | | | |
|---|---|---|---|---|
| (ppm) | 250 | 125 | 63 | 0 |
| 500 | 5.0 (14.9) | 25.0 (51.0) | 30.0 (59.5) | 85.0 |
| 125 | 15.0 (16.6) | 30.0 (57.0) | 30.0 (66.5) | 95.0 |
| 0 | 17.5 | 60.0 | 70.0 | — |

TABLE 1-33

| Concentration of metrafefone | Concentration of Compound No. 4 (ppm) | | | |
|---|---|---|---|---|
| (ppm) | 125 | 63 | 31 | 0 |
| 0.03 | 0 (1.8) | 0 (2.6) | 0 (2.6) | 35.0 |
| 0.015 | 0 (2.0) | 0 (3.0) | 0 (3.0) | 40.0 |
| 0.0075 | 2.0 (5.0) | 0 (7.5) | 0 (7.5) | 100 |
| 0 | 5.0 | 7.5 | 7.5 | — |

TABLE 1-34

| Concentration of metrafenone | Concentration of Compound No. 5 (ppm) | | | |
|---|---|---|---|---|
| (ppm) | 125 | 63 | 31 | 0 |
| 0.03 | 0 (0.88) | 0 (0.88) | 0 (4.4) | 35.0 |
| 0.015 | 0 (1.0) | 0 (1.0) | 0 (5.0) | 40.0 |

TABLE 1-34-continued

| Concentration of metrafenone (ppm) | Concentration of Compound No. 5 (ppm) | | | |
|---|---|---|---|---|
| | 125 | 63 | 31 | 0 |
| 0.0075 | 0 (2.5) | 2.0 (2.5) | 3.0 (12.5) | 100 |
| 0 | 2.5 | 2.5 | 12.5 | — |

TABLE 1-35

| Concentration of metrafenone (ppm) | Concentration of Compound No. 8 (ppm) | | |
|---|---|---|---|
| | 125 | 63 | 0 |
| 0.03 | 7.0 (10.5) | 20.0 (21.0) | 35.0 |
| 0.0075 | 10.0 (30.0) | 35.0 (60.0) | 100 |
| 0 | 30.0 | 60.0 | — |

TABLE 1-36

| Concentration of metrafenone (ppm) | Concentration of Compound No. 11 (ppm) | | | |
|---|---|---|---|---|
| | 250 | 125 | 63 | 0 |
| 0.03 | 0 (4.4) | 3.0 (8.8) | 15.0 (21.0) | 35.0 |
| 0.015 | 0 (5.0) | 10.0 (10.0) | 20.0 (24.0) | 40.0 |
| 0.0075 | 0 (12.5) | 10.0 (25.0) | 20.0 (60.0) | 100 |
| 0 | 12.5 | 25.0 | 60.0 | — |

TABLE 1-37

| Concentration of fenpropidin (ppm) | Concentration of Compound No. 4 (ppm) | | | |
|---|---|---|---|---|
| | 63 | 31 | 16 | 0 |
| 50 | 0 (0.02) | 0 (0.02) | 0 (0.08) | 1.0 |
| 25 | 0 (0.03) | 0 (0.04) | 0 (0.15) | 2.0 |
| 12.5 | 0 (0.41) | 0 (0.55) | 0 (2.1) | 27.5 |
| 0 | 1.5 | 2.0 | 7.5 | — |

TABLE 1-38

| Concentration of fenpropidin (ppm) | Concentration of Compound No. 5 (ppm) | | | |
|---|---|---|---|---|
| | 63 | 31 | 16 | 0 |
| 50 | 0 (0.02) | 0 (0.03) | 0 (0.15) | 1.0 |
| 25 | 0 (0.03) | 0 (0.05) | 0 (0.3) | 2.0 |
| 12.5 | 0 (0.41) | 0 (0.69) | 0 (4.1) | 27.5 |
| 0 | 1.5 | 2.5 | 15.0 | — |

TABLE 1-39

| Concentration of fenpropidin (ppm) | Concentration of Compound No. 8 (ppm) | | | |
|---|---|---|---|---|
| | 250 | 125 | 63 | 0 |
| 50 | 0 (0.13) | 0 (0.15) | 0 (0.18) | 1.0 |
| 25 | 0 (0.25) | 0 (0.30) | 0 (0.35) | 2.0 |
| 12.5 | 0 (3.4) | 0 (4.1) | 0 (4.8) | 27.5 |
| 0 | 12.5 | 15.0 | 17.5 | — |

TABLE 1-40

| Concentration of fenpropidin (ppm) | Concentration of Compound No. 11 (ppm) | | | |
|---|---|---|---|---|
| | 250 | 125 | 63 | 0 |
| 50 | 0 (0.35) | 0 (0.60) | 0 (0.85) | 1.0 |
| 25 | 0 (0.70) | 0 (1.2) | 0 (1.7) | 2.0 |
| 12.5 | 0 (9.6) | 0 (16.5) | 0 (23.4) | 27.5 |
| 0 | 35.0 | 60.0 | 85.0 | — |

TABLE 1-41

| Concentration of fenpropimorph (ppm) | Concentration of Compound No. 4 (ppm) | | | |
|---|---|---|---|---|
| | 250 | 125 | 63 | 0 |
| 25 | 0 (0.05) | 0 (0.33) | 0 (0.72) | 9.1 |
| 12.5 | 0 (0.22) | 0 (1.3) | 0 (2.9) | 36.4 |
| 0 | 0.6 | 3.6 | 7.9 | — |

TABLE 1-42

| Concentration of fenpropimorph (ppm) | Concentration of Compound No. 5 (ppm) | | |
|---|---|---|---|
| | 250 | 125 | 0 |
| 25 | 0 (0.05) | 0 (0.05) | 9.1 |
| 12.5 | 0 (0.22) | 0 (0.22) | 36.4 |
| 0 | 0.6 | 0.6 | — |

TABLE 1-43

| Concentration of fenpropimorph (ppm) | Concentration of Compound No. 8 (ppm) | | | |
|---|---|---|---|---|
| | 250 | 125 | 63 | 0 |
| 25 | 0 (0.83) | 0 (1.4) | 0 (1.9) | 9.1 |
| 12.5 | 0 (3.3) | 0 (5.5) | 0 (7.7) | 36.4 |
| 0 | 9.1 | 15.2 | 21.2 | — |

TABLE 1-44

| Concentration of fenpropimorph (ppm) | Concentration of Compound No. 11 (ppm) | | | |
|---|---|---|---|---|
| | 250 | 125 | 63 | 0 |
| 25 | 0 (1.4) | 0 (1.9) | 0 (2.2) | 9.1 |
| 12.5 | 0 (5.5) | 0 (7.7) | 0 (8.8) | 36.4 |
| 0 | 15.2 | 21.2 | 24.2 | — |

TABLE 1-45

| Concentration of fosetyl-Al (ppm) | Concentration of Compound No. 4 (ppm) | | | |
|---|---|---|---|---|
| | 63 | 31 | 16 | 0 |
| 1000 | 0 (3.9) | 0 (4.9) | 3.0 (12.2) | 97.5 |
| 0 | 4.0 | 5.0 | 12.5 | — |

TABLE 1-46

| Concentration of fosetyl-Al (ppm) | Concentration of Compound No. 5 (ppm) | | |
|---|---|---|---|
| | 63 | 31 | 0 |
| 1000 | 2.0 (2.9) | 10.0 (14.6) | 97.5 |
| 0 | 3.0 | 15.0 | — |

TABLE 1-47

| Concentration of fosetyl-Al (ppm) | Concentration of Compound No. 8 (ppm) | | | |
|---|---|---|---|---|
| | 250 | 125 | 63 | 0 |
| 500 | 0 (19.5) | 0 (24.4) | 20.0 (43.9) | 97.5 |
| 0 | 20.0 | 25.0 | 45.0 | — |

TABLE 1-48

| Concentration of fosetyl-Al (ppm) | Concentration of Compound No. 11 (ppm) | | | |
|---|---|---|---|---|
| | 250 | 125 | 63 | 0 |
| 1000 | 13.0 (39.0) | 15.0 (48.8) | 50.0 (87.8) | 97.5 |
| 500 | 15.0 (39.0) | 30.0 (48.8) | 50.0 (87.8) | 97.5 |
| 0 | 40.0 | 50.0 | 90.0 | — |

TABLE 1-49

| Concentration of flutolanil (ppm) | Concentration of Compound No. 4 (ppm) | | | |
|---|---|---|---|---|
| | 63 | 31 | 16 | 0 |
| 500 | 0 (0.3) | 0 (0.38) | 0 (0.94) | 7.5 |
| 0 | 4.0 | 5.0 | 12.5 | — |

TABLE 1-50

| Concentration of flutolanil (ppm) | Concentration of Compound No. 5 (ppm) | | |
|---|---|---|---|
| | 63 | 16 | 0 |
| 1000 | 0 (0.38) | 3.0 (3.1) | 12.5 |
| 0 | 3.0 | 25.0 | — |

TABLE 1-51

| Concentration of flutolanil (ppm) | Concentration of Compound No. 8 (ppm) | | |
|---|---|---|---|
| | 250 | 125 | 0 |
| 1000 | 0 (2.5) | 0 (3.1) | 12.5 |
| 0 | 20.0 | 25.0 | — |

TABLE 1-52

| Concentration of quinoxyfen (ppm) | Concentration of Compound No. 4 (ppm) | | | |
|---|---|---|---|---|
| | 63 | 31 | 16 | 0 |
| 0.25 | 0 (0.75) | 0 (4.9) | 0 (9.4) | 75.0 |
| 0.125 | 0 (0.78) | 0 (5.0) | 8.0 (9.7) | 77.5 |
| 0 | 1.0 | 6.5 | 12.5 | — |

TABLE 1-53

| Concentration of quinoxyfen (ppm) | Concentration of Compound No. 5 (ppm) | | |
|---|---|---|---|
| | 63 | 31 | 0 |
| 0.25 | 0 (0.38) | 0 (1.9) | 75.0 |
| 0.125 | 0 (0.39) | 0 (1.9) | 77.5 |
| 0 | 0.5 | 2.5 | — |

TABLE 1-54

| Concentration of quinoxyfen (ppm) | Concentration of Compound No. 7 (ppm) | | | |
|---|---|---|---|---|
| | 31 | 16 | 8 | 0 |
| 0.25 | 0 (3.0) | 0 (18.8) | 20.0 (22.5) | 75.0 |
| 0.06 | 0 (3.2) | 15.0 (20.0) | 29.0 (24.0) | 80.0 |
| 0 | 4.0 | 25.0 | 30.0 | — |

TABLE 1-55

| Concentration of quinoxyfen (ppm) | Concentration of Compound No. 11 (ppm) | | | |
|---|---|---|---|---|
| | 250 | 125 | 63 | 0 |
| 0.25 | 0 (13.1) | 20.0 (45.0) | 30.0 (52.5) | 75.0 |
| 0.125 | 0 (13.6) | 25.0 (46.5) | 35.0 (54.3) | 77.5 |
| 0.06 | 3.0 (14.0) | 25.0 (48.0) | 40.0 (56.0) | 80.0 |
| 0 | 17.5 | 60.0 | 70.0 | — |

TABLE 1-56

| Concentration of metconazole (ppm) | Concentration of Compound No. 2 (ppm) | | | |
|---|---|---|---|---|
| | 500 | 250 | 125 | 0 |
| 0.03 | 10.0 (38.5) | 10.0 (52.3) | 10.0 (53.6) | 55.0 |
| 0.015 | 40.0 (63.0) | 40.0 (85.5) | 60.0 (87.8) | 90.0 |
| 0.0075 | 65.0 (66.5) | 75.0 (90.3) | 80.0 (92.6) | 95.0 |
| 0 | 70.0 | 95.0 | 97.5 | — |

TABLE 1-57

| Concentration of metconazole (ppm) | Concentration of Compound No. 4 (ppm) | | | |
|---|---|---|---|---|
| | 63 | 31 | 16 | 0 |
| 0.03 | 0 (6.9) | 3.0 (9.6) | 3.0 (11.0) | 55.0 |
| 0.015 | 3.0 (11.3) | 3.0 (15.8) | 3.0 (18.0) | 90.0 |
| 0.0075 | 5.0 (11.9) | 5.0 (16.6) | 5.0 (19.0) | 95.0 |
| 0 | 12.5 | 17.5 | 20.0 | — |

TABLE 1-58

| Concentration of metconazole (ppm) | Concentration of Compound No. 5 (ppm) | | | |
|---|---|---|---|---|
| | 63 | 31 | 16 | 0 |
| 0.015 | 10.0 (24.8) | 5.0 (36.0) | 8.0 (38.3) | 90.0 |
| 0.0075 | 10.0 (26.1) | 10.0 (38.0) | 10.0 (40.4) | 95.0 |
| 0 | 27.5 | 40.0 | 42.5 | — |

TABLE 1-59

| Concentration of metconazole (ppm) | Concentration of Compound No. 8 (ppm) | | | |
|---|---|---|---|---|
| | 250 | 125 | 63 | 0 |
| 0.03 | 5.0 (35.8) | 10.0 (49.5) | 20.0 (52.3) | 55.0 |
| 0.015 | 20.0 (58.5) | 50.0 (81.0) | 50.0 (85.5) | 90.0 |
| 0.0075 | 40.0 (61.8) | 55.0 (85.5) | 65.0 (90.3) | 95.0 |
| 0 | 65.0 | 90.0 | 95.0 | — |

TABLE 1-60

| Concentration of metconazole (ppm) | Concentration of Compound No. 11 (ppm) | | |
|---|---|---|---|
| | 250 | 125 | 0 |
| 0.03 | 30.0 (35.8) | 45.0 (52.3) | 55.0 |
| 0.015 | 30.0 (58.5) | 60.0 (85.5) | 90.0 |
| 0.0075 | 40.0 (61.8) | 65.0 (90.3) | 95.0 |
| 0 | 65.0 | 95.0 | — |

TABLE 1-61

| Concentration of tricyclazole (ppm) | Concentration of Compound No. 2 (ppm) | | |
|---|---|---|---|
| | 250 | 125 | 0 |
| 500 | 20.0 (37.5) | 25.0 (45.0) | 50.0 |
| 50 | 15.0 (16.9) | 15.0 (20.3) | 22.5 |
| 0 | 75.0 | 90.0 | — |

TABLE 1-62

| Concentration of tricyclazole (ppm) | Concentration of Compound No. 4 (ppm) | | |
|---|---|---|---|
| | 63 | 16 | 0 |
| 500 | 0 (2.5) | 5.0 (6.3) | 50.0 |
| 0 | 5.0 | 12.5 | — |

TABLE 1-63

| Concentration of tricyclazole (ppm) | Concentration of Compound No. 5 (ppm) | | |
|---|---|---|---|
| | 31 | 16 | 0 |
| 500 | 5.0 (15.0) | 0 (20.0) | 50.0 |
| 50 | 5.0 (6.8) | 5.0 (9.0) | 22.5 |
| 0 | 30.0 | 40.0 | — |

TABLE 1-64

| Concentration of tricyclazole (ppm) | Concentration of Compound No. 8 (ppm) | | |
|---|---|---|---|
| | 125 | 63 | 0 |
| 500 | 10.0 (12.5) | 5.0 (20.0) | 50.0 |
| 50 | 5.0 (5.6) | 0 (9.0) | 22.5 |
| 0 | 25.0 | 40.0 | — |

TABLE 1-65

| Concentration of tricyclazole (ppm) | Concentration of Compound No. 11 (ppm) | | |
|---|---|---|---|
| | 125 | 63 | 0 |
| 500 | 5.0 (40.0) | 5.0 (43.8) | 50.0 |
| 0 | 80.0 | 87.5 | — |

TABLE 1-66

| Concentration of dimoxystrobin (ppm) | Concentration of Compound No. 2 (ppm) | |
|---|---|---|
| | 250 | 0 |
| 5 | 3.0 (3.8) | 5.0 |
| 0 | 75.0 | — |

TABLE 1-67

| Concentration of dimoxystrobin (ppm) | Concentration of Compound No. 4 (ppm) | | | |
|---|---|---|---|---|
| | 63 | 31 | 16 | 0 |
| 5 | 0 (0.25) | 0 (0.50) | 0 (0.63) | 5.0 |
| 0 | 5.0 | 10.0 | 12.5 | — |

TABLE 1-68

| Concentration of dimoxystrobin (ppm) | Concentration of Compound No. 5 (ppm) | | |
|---|---|---|---|
| | 63 | 31 | 0 |
| 5 | 0 (0.75) | 0 (1.5) | 5.0 |
| 0 | 15.0 | 30.0 | — |

TABLE 1-69

| Concentration of dimoxystrobin (ppm) | Concentration of Compound No. 8 (ppm) | | |
|---|---|---|---|
| | 250 | 63 | 0 |
| 5 | 0 (1.0) | 0 (2.0) | 5.0 |
| 0 | 20.0 | 40.0 | — |

TABLE 1-70

| Concentration of dimoxystrobin | Concentration of Compound No. 11 (ppm) | | |
|---|---|---|---|
| (ppm) | 250 | 125 | 0 |
| 5 | 0 (0.38) | 3.0 (4.3) | 5.0 |
| 0 | 7.5 | 85.0 | — |

TABLE 1-71

| Concentration of sulfur | Concentration of Compound No. 2 (ppm) | | | |
|---|---|---|---|---|
| (ppm) | 500 | 250 | 125 | 0 |
| 500 | 5.0 (28.0) | 5.0 (38.0) | 25.0 (39.0) | 40.0 |
| 50 | 55.0 (68.3) | 60.0 (92.6) | 65.0 (95.1) | 97.5 |
| 0 | 70.0 | 95.0 | 97.5 | — |

TABLE 1-72

| Concentration of sulfur | Concentration of Compound No. 4 (ppm) | | | |
|---|---|---|---|---|
| (ppm) | 63 | 31 | 16 | 0 |
| 500 | 0 (5.0) | 0 (7.0) | 5.0 (8.0) | 40.0 |
| 50 | 3.0 (12.2) | 5.0 (17.1) | 15.0 (19.5) | 97.5 |
| 0 | 12.5 | 17.5 | 20.0 | — |

TABLE 1-73

| Concentration of sulfur | Concentration of Compound No. 5 (ppm) | | | |
|---|---|---|---|---|
| (ppm) | 63 | 31 | 16 | 0 |
| 500 | 0 (11.0) | 0 (16.0) | 1.0 (17.0) | 40.0 |
| 50 | 10.0 (26.8) | 15.0 (39.0) | 30.0 (41.4) | 97.5 |
| 0 | 27.5 | 40.0 | 42.5 | — |

TABLE 1-74

| Concentration of sulfur | Concentration of Compound No. 8 (ppm) | | | |
|---|---|---|---|---|
| (ppm) | 250 | 125 | 63 | 0 |
| 500 | 0 (26.0) | 0 (36.0) | 5.0 (38.0) | 40.0 |
| 50 | 15.0 (63.4) | 15.0 (87.8) | 60.0 (92.6) | 97.5 |
| 0 | 65.0 | 90.0 | 95.0 | — |

TABLE 1-75

| Concentration of sulfur | Concentration of Compound No. 11 (ppm) | | | |
|---|---|---|---|---|
| (ppm) | 250 | 125 | 63 | 0 |
| 500 | 3.0 (26.0) | 3.0 (38.0) | 5.0 (39.0) | 40.0 |
| 50 | 10.0 (63.4) | 10.0 (92.6) | 10.0 (95.1) | 97.5 |
| 0 | 65.0 | 95.0 | 97.5 | — |

TABLE 1-76

| Concentration of kasugamycin | Concentration of Compound No. 2 (ppm) | | | |
|---|---|---|---|---|
| (ppm) | 500 | 250 | 125 | 0 |
| 500 | 5.0 (38.5) | 5.0 (52.3) | 15.0 (53.6) | 55.0 |
| 50 | 60.0 (68.3) | 60.0 (92.6) | 65.0 (95.1) | 97.5 |
| 0 | 70.0 | 95.0 | 97.5 | — |

TABLE 1-77

| Concentration of kasugamycin | Concentration of Compound No. 4 (ppm) | | | |
|---|---|---|---|---|
| (ppm) | 63 | 31 | 16 | 0 |
| 500 | 5.0 (6.9) | 5.0 (9.6) | 10.0 (11.0) | 55.0 |
| 50 | 12.0 (12.2) | 10.0 (17.1) | 15.0 (19.5) | 97.5 |
| 0 | 12.5 | 17.5 | 20.0 | — |

TABLE 1-78

| Concentration of kasugamycin | Concentration of Compound No. 5 (ppm) | | | |
|---|---|---|---|---|
| (ppm) | 63 | 31 | 16 | 0 |
| 500 | 5.0 (15.1) | 5.0 (22.0) | 10.0 (23.4) | 55.0 |
| 50 | 10.0 (26.8) | 35.0 (39.0) | 40.0 (41.4) | 97.5 |
| 0 | 27.5 | 40.0 | 42.5 | — |

TABLE 1-79

| Concentration of kasugamycin | Concentration of Compound No. 8 (ppm) | | | |
|---|---|---|---|---|
| (ppm) | 250 | 125 | 63 | 0 |
| 500 | 5.0 (35.8) | 10.0 (49.5) | 20.0 (52.3) | 55.0 |
| 50 | 20.0 (63.4) | 30.0 (87.8) | 30.0 (92.6) | 97.5 |
| 0 | 65.0 | 90.0 | 95.0 | — |

TABLE 1-80

| Concentration of kasugamycin | Concentration of Compound No. 11 (ppm) | | | |
|---|---|---|---|---|
| (ppm) | 250 | 125 | 63 | 0 |
| 500 | 0 (35.8) | 0 (52.3) | 5.0 (53.6) | 55.0 |
| 50 | 10.0 (63.4) | 10.0 (92.6) | 20.0 (95.1) | 97.5 |
| 0 | 65.0 | 95.0 | 97.5 | — |

TABLE 1-81

| Concentration of compound β | Concentration of Compound No. 2 (ppm) | | |
|---|---|---|---|
| (ppm) | 250 | 125 | 0 |
| 100 | 5 (15) | 5 (18) | 20.0 |
| 10 | 70 (71.3) | 60 (85.5) | 95.0 |
| 0 | 75.0 | 90.0 | — |

TABLE 1-82

| Concentration of compound β (ppm) | Concentration of Compound No. 4 (ppm) | |
|---|---|---|
| | 63 | 0 |
| 100 | 0 (1.8) | 35.0 |
| 0 | 5.0 | — |

TABLE 1-83

| Concentration of compound β (ppm) | Concentration of Compound No. 5 (ppm) | | |
|---|---|---|---|
| | 31 | 16 | 0 |
| 100 | 5.0 (6.0) | 5.0 (8.0) | 20.0 |
| 10 | 5.0 (28.5) | 0 (38.0) | 95.0 |
| 0 | 30.0 | 40.0 | — |

TABLE 1-84

| Concentration of compound β (ppm) | Concentration of Compound No. 8 (ppm) | | | |
|---|---|---|---|---|
| | 250 | 125 | 63 | 0 |
| 10 | 15.0 (19.0) | 15.0 (23.8) | 30.0 (38.0) | 95.0 |
| 0 | 20.0 | 25.0 | 40.0 | — |

TABLE 1-85

| Concentration of compound β (ppm) | Concentration of Compound No. 11 (ppm) | | | |
|---|---|---|---|---|
| | 250 | 125 | 63 | 0 |
| 100 | 0 (1.5) | 3 (16.0) | 0 (17.5) | 20.0 |
| 10 | 5 (7.1) | 10 (76.0) | 5 (83.1) | 95.0 |
| 0 | 7.5 | 80.0 | 87.5 | — |

TABLE 1-86

| Concentration of compound A (ppm) | Concentration of Compound No. 4 (ppm) | | | |
|---|---|---|---|---|
| | 63 | 31 | 16 | 0 |
| 0.25 | 0 (6.0) | 1.0 (7.0) | 3.0 (7.0) | 40.0 |
| 0.125 | 1.0 (9.8) | 3.0 (11.4) | 5.0 (11.4) | 65.0 |
| 0.063 | 1.0 (13.5) | 3.0 (15.8) | 7.0 (15.8) | 90.0 |
| 0 | 15.0 | 17.5 | 17.5 | — |

TABLE 1-87

| Concentration of compound A (ppm) | Concentration of Compound No. 5 (ppm) | | | |
|---|---|---|---|---|
| | 63 | 31 | 16 | 0 |
| 0.125 | 5.0 (6.5) | 8.0 (11.4) | 15.0 (16.3) | 65.0 |
| 0.063 | 5.0 (9.0) | 10.0 (15.8) | 15.0 (22.5) | 90.0 |
| 0 | 10.0 | 17.5 | 25.0 | — |

TABLE 1-88

| Concentration of compound A (ppm) | Concentration of Compound No. 8 (ppm) | | | |
|---|---|---|---|---|
| | 250 | 125 | 63 | 0 |
| 0.125 | 7.0 (26.0) | 10.0 (35.8) | 10.0 (39.0) | 65 |
| 0.063 | 8.0 (36.0) | 20.0 (49.5) | 25.0 (54.0) | 90 |
| 0 | 40.0 | 55.0 | 60.0 | — |

TABLE 1-89

| Concentration of compound A (ppm) | Concentration of Compound No. 11 (ppm) | |
|---|---|---|
| | 125 | 0 |
| 0.25 | 10.0 (14.0) | 40.0 |
| 0.125 | 10.0 (22.8) | 65.0 |
| 0.063 | 15.0 (31.5) | 90.0 |
| 0 | 35.0 | — |

TABLE 1-90

| Concentration of compound B (ppm) | Concentration of Compound No. 4 (ppm) | | |
|---|---|---|---|
| | 63 | 31 | 0 |
| 0.5 | 3.0 (4.5) | 0 (5.3) | 30.0 |
| 0.25 | 3.0 (6.0) | 0 (7.0) | 40.0 |
| 0.125 | 3.0 (7.5) | 5 (8.8) | 50.0 |
| 0 | 15.0 | 17.5 | — |

TABLE 1-91

| Concentration of compound B (ppm) | Concentration of Compound No. 5 (ppm) | | | |
|---|---|---|---|---|
| | 63 | 31 | 16 | 0 |
| 0.5 | 0 (3.0) | 2.0 (5.3) | 5.0 (7.5) | 30.0 |
| 0 | 10.0 | 17.5 | 25.0 | — |

TABLE 1-92

| Concentration of compound B (ppm) | Concentration of Compound No. 8 (ppm) | | | |
|---|---|---|---|---|
| | 250 | 125 | 63 | 0 |
| 0.25 | 10.0 (16.0) | 10.0 (22.0) | 20.0 (24.0) | 40.0 |
| 0.125 | 10.0 (20.0) | 20.0 (27.5) | 25.0 (30.0) | 50.0 |
| 0 | 40.0 | 55.0 | 60.0 | — |

TABLE 1-93

| Concentration of compound B (ppm) | Concentration of Compound No. 11 (ppm) | | | |
|---|---|---|---|---|
| | 250 | 125 | 63 | 0 |
| 0.5 | 2.0 (6.8) | 3.0 (10.5) | 5.0 (13.5) | 30.0 |
| 0.25 | 3.0 (9.0) | 5.0 (14.0) | 15.0 (18.0) | 40.0 |
| 0.125 | 3.0 (11.3) | 10.0 (17.5) | 20.0 (22.5) | 50.0 |
| 0 | 22.5 | 35.0 | 45.0 | — |

TABLE 1-94

| Concentration of compound C (ppm) | Concentration of Compound No. 4 (ppm) | | |
|---|---|---|---|
| | 63 | 31 | 0 |
| 0.5 | 0 (0.90) | 0 (1.1) | 6.0 |
| 0.25 | 0 (4.5) | 3.0 (5.3) | 30.0 |
| 0.125 | 0 (5.6) | 5.0 (6.6) | 37.5 |
| 0 | 15.0 | 17.5 | — |

TABLE 1-95

| Concentration of compound C (ppm) | Concentration of Compound No. 5 (ppm) | | | |
|---|---|---|---|---|
| | 63 | 31 | 16 | 0 |
| 0.5 | 0 (0.60) | 0 (1.1) | 0 (1.5) | 6.0 |
| 0.25 | 0 (3.0) | 0 (5.3) | 3.0 (7.5) | 30.0 |
| 0.125 | 3.0 (3.8) | 5.0 (6.6) | 5.0 (9.4) | 37.5 |
| 0 | 10.0 | 17.5 | 25.0 | — |

TABLE 1-96

| Concentration of compound C (ppm) | Concentration of Compound No. 8 (ppm) | | | |
|---|---|---|---|---|
| | 250 | 125 | 63 | 0 |
| 0.5 | 0 (2.4) | 0 (3.3) | 0 (3.6) | 6.0 |
| 0.125 | 10.0 (15.0) | 13.0 (20.6) | 15.0 (22.5) | 37.5 |
| 0 | 40.0 | 55.0 | 60.0 | — |

TABLE 1-97

| Concentration of compound C (ppm) | Concentration of Compound No. 11 (ppm) | | |
|---|---|---|---|
| | 125 | 63 | 0 |
| 0.5 | 0 (2.1) | 0 (2.7) | 6.0 |
| 0.25 | 0 (10.5) | 8.0 (13.5) | 30.0 |
| 0.125 | 5.0 (13.1) | 10.0 (16.9) | 37.5 |
| 0 | 35.0 | 45.0 | — |

TABLE 1-98

| Concentration of compound D (ppm) | Concentration of Compound No. 4 (ppm) | | |
|---|---|---|---|
| | 125 | 63 | 0 |
| 0.25 | 0 (0.63) | 0 (0.94) | 12.5 |
| 0.125 | 0 (0.75) | 0 (1.1) | 15.0 |
| 0.06 | 0 (1.4) | 2.0 (2.1) | 27.5 |
| 0 | 5.0 | 7.5 | — |

TABLE 1-99

| Concentration of compound D (ppm) | Concentration of Compound No. 5 (ppm) | | |
|---|---|---|---|
| | 125 | 31 | 0 |
| 0.25 | 0 (0.31) | 0 (1.6) | 12.5 |
| 0.125 | 0 (0.38) | 0 (1.9) | 15.0 |
| 0.06 | 0 (0.69) | 2 (3.4) | 27.5 |
| 0 | 2.5 | 12.5 | — |

TABLE 1-100

| Concentration of compound D (ppm) | Concentration of Compound No. 8 (ppm) | | | |
|---|---|---|---|---|
| | 250 | 125 | 63 | 0 |
| 0.25 | 0 (1.3) | 3.0 (3.8) | 3.0 (7.5) | 12.5 |
| 0.06 | 2.0 (2.8) | 3 (8.3) | 10.0 (16.5) | 27.5 |
| 0 | 10.0 | 30.0 | 60.0 | — |

TABLE 1-101

| Concentration of compound D (ppm) | Concentration of Compound No. 11 (ppm) | | |
|---|---|---|---|
| | 250 | 63 | 0 |
| 0.25 | 0 (1.6) | 5.0 (7.5) | 12.5 |
| 0.125 | 0 (1.9) | 5.0 (9.0) | 15.0 |
| 0.06 | 0 (3.4) | 8.0 (16.5) | 27.5 |
| 0 | 12.5 | 60.0 | — |

TEST EXAMPLE 2

Test on Preventive Effect Against Cucumber Powdery Mildew

Cucumber (cultivar: Suyo) was cultivated in a plastic pot having a diameter of 7.5 cm, and when it reached 1.5-leaf stage, a mixed chemical solution having the respective sample compounds adjusted to prescribed concentrations, was applied by a spray gun in an amount of 10 ml per seedling. After the chemical solution dried, a suspension of conidia of *Sphaerotheca fuliginea* was sprayed and inoculated and maintained in a constant temperature chamber at 20° C. From 7 to 12 days after the inoculation, the area of sporulation was investigated, and the diseased area ratio to non-treated section was obtained in the same manner as in Test Example 1. The results are shown in Tables 2-1 to 2-112.

Further, the theoretical value was calculated by a Colby's formula and shown in brackets ( ) in Tables 2-1 to 2-112. Since the diseased area ratio to non-treated section (experimental value) is lower than the theoretical value, the composition of the present invention can be said to have a synergistic effect.

TABLE 2-1

| Concentration of difenoconazole (ppm) | Concentration of Compound No. 4 (ppm) | | |
|---|---|---|---|
| | 4 | 1 | 0 |
| 8 | 0 (0.59) | 1.0 (2.5) | 31.3 |
| 0 | 1.9 | 8.1 | — |

TABLE 2-2

| Concentration of difenoconazole (ppm) | Concentration of Compound No. 5 (ppm) | | |
|---|---|---|---|
| | 2 | 1 | 0 |
| 16 | 0 (0.18) | 0 (1.5) | 9.4 |
| 8 | 0 (0.59) | 0 (4.9) | 31.3 |
| 0 | 1.9 | 15.6 | — |

TABLE 2-3

| Concentration of difenoconazole (ppm) | Concentration of Compound No. 8 (ppm) | | | |
|---|---|---|---|---|
| | 16 | 8 | 4 | 0 |
| 31 | 0 (0.25) | 0 (0.25) | 0 (0.66) | 8.1 |
| 16 | 0 (0.29) | 0 (0.29) | 0 (0.76) | 9.4 |
| 0 | 3.1 | 3.1 | 8.1 | — |

TABLE 2-4

| Concentration of difenoconazole (ppm) | Concentration of Compound No. 11 (ppm) | | | |
|---|---|---|---|---|
| | 4 | 2 | 1 | 0 |
| 31 | 0 (0.05) | 0 (0.15) | 0 (0.51) | 8.1 |
| 16 | 0 (0.06) | 0 (0.18) | 0 (0.59) | 9.4 |
| 8 | 0 (0.19) | 0 (0.59) | 0 (2.0) | 31.3 |
| 0 | 0.6 | 1.9 | 6.3 | — |

TABLE 2-5

| Concentration of cyazofamid (ppm) | Concentration of Compound No. 4 (ppm) | |
|---|---|---|
| | 2 | 0 |
| 125 | 1.0 (1.4) | 57.5 |
| 63 | 1.0 (2.0) | 80.0 |
| 0 | 7.5 | — |

TABLE 2-6

| Concentration of cyazofamid (ppm) | Concentration of Compound No. 5 (ppm) | |
|---|---|---|
| | 2 | 0 |
| 125 | 0 (0.29) | 57.5 |
| 0 | 0.5 | — |

TABLE 2-7

| Concentration of cyazofamid (ppm) | Concentration of Compound No. 8 (ppm) | | | |
|---|---|---|---|---|
| | 8 | 4 | 2 | 0 |
| 125 | 5.0 (23.0) | 8.0 (20.1) | 15.0 (25.9) | 57.5 |
| 31 | 10.0 (32.0) | 10.0 (28.0) | 15.0 (36.0) | 80.0 |
| 0 | 40.0 | 35.0 | 45.0 | — |

TABLE 2-8

| Concentration of cyazofamid (ppm) | Concentration of Compound No. 11 (ppm) | | |
|---|---|---|---|
| | 8 | 4 | 0 |
| 63 | 1.0 (2.8) | 2.0 (3.5) | 70.0 |
| 31 | 0 (3.4) | 2.0 (4.3) | 85.0 |
| 0 | 4.0 | 5.0 | — |

TABLE 2-9

| Concentration of mepanipyrim (ppm) | Concentration of Compound No. 4 (ppm) | | |
|---|---|---|---|
| | 4 | 2 | 0 |
| 125 | 0 (0.013) | 0 (0.038) | 0.5 |
| 63 | 0 (0.013) | 0 (0.038) | 0.5 |
| 31 | 0 (0.25) | 0 (0.75) | 10.0 |
| 0 | 2.5 | 7.5 | — |

TABLE 2-10

| Concentration of mepanipyrim (ppm) | Concentration of Compound No. 5 (ppm) | | |
|---|---|---|---|
| | 4 | 2 | 0 |
| 125 | 0 (0.0025) | 0 (0.015) | 0.5 |
| 63 | 0 (0.0025) | 0 (0.015) | 0.5 |
| 31 | 0 (0.05) | 0 (0.3) | 10.0 |
| 0 | 0.5 | 3.0 | — |

TABLE 2-11

| Concentration of mepanipyrim (ppm) | Concentration of Compound No. 8 (ppm) | | |
|---|---|---|---|
| | 4 | 2 | 0 |
| 125 | 0 (0.18) | 0 (0.23) | 0.5 |
| 63 | 0 (0.18) | 0 (0.23) | 0.5 |
| 0 | 35.0 | 45.0 | — |

TABLE 2-12

| Concentration of mepanipyrim (ppm) | Concentration of Compound No. 11 (ppm) | | | |
|---|---|---|---|---|
| | 8 | 4 | 2 | 0 |
| 125 | 0 (0.02) | 0 (0.03) | 0 (0.03) | 0.5 |
| 31 | 0 (1.6) | 0 (2.0) | 0 (2.6) | 40.0 |
| 0 | 4.0 | 5.0 | 6.5 | — |

TABLE 2-13

| Concentration of azoxystrobin (ppm) | Concentration of Compound No. 4 (ppm) | |
|---|---|---|
| | 4 | 0 |
| 125 | 0 (0.88) | 35.0 |
| 63 | 0 (0.88) | 35.0 |
| 31 | 0 (0.94) | 37.5 |
| 0 | 2.5 | — |

TABLE 2-14

| Concentration of azoxystrobin (ppm) | Concentration of Compound No. 5 (ppm) | | |
|---|---|---|---|
| | 4 | 2 | 0 |
| 63 | 0 (0.18) | 0 (1.1) | 35.0 |
| 31 | 0 (0.19) | 0 (1.1) | 37.5 |
| 0 | 0.5 | 3.0 | — |

TABLE 2-15

| Concentration of azoxystrobin (ppm) | Concentration of Compound No. 8 (ppm) | |
|---|---|---|
| | 4 | 0 |
| 125 | 12.0 (12.3) | 35.0 |
| 63 | 12.0 (12.3) | 35.0 |
| 31 | 13.0 (13.1) | 37.5 |
| 0 | 35.0 | — |

TABLE 2-16

| Concentration of azoxystrobin (ppm) | Concentration of Compound No. 11 (ppm) | | | |
|---|---|---|---|---|
| | 8 | 4 | 2 | 0 |
| 63 | 0 (2.2) | 0 (2.8) | 3.0 (3.6) | 55.0 |
| 31 | 1.0 (2.2) | 1.0 (2.8) | 3.0 (3.6) | 55.0 |
| 0 | 4.0 | 5.0 | 6.5 | — |

TABLE 2-17

| Concentration of folpet (ppm) | Concentration of Compound No. 4 (ppm) | | |
|---|---|---|---|
| | 4 | 1 | 0 |
| 500 | 0 (4.1) | 6.3 (12.7) | 81.3 |
| 125 | 1.3 (4.2) | 10.0 (13.2) | 84.4 |
| 0 | 5.0 | 15.6 | — |

TABLE 2-18

| Concentration of folpet (ppm) | Concentration of Compound No. 5 (ppm) | | |
|---|---|---|---|
| | 4 | 1 | 0 |
| 500 | 0 (3.1) | 10.0 (12.7) | 81.3 |
| 250 | 1.3 (3.2) | 10.0 (13.2) | 84.4 |
| 0 | 3.8 | 15.6 | — |

TABLE 2-19

| Concentration of folpet (ppm) | Concentration of Compound No. 7 (ppm) | | |
|---|---|---|---|
| | 2 | 1 | 0 |
| 250 | 12.5 (63.3) | 18.8 (68.6) | 84.4 |
| 0 | 75.0 | 81.3 | — |

TABLE 2-20

| Concentration of folpet (ppm) | Concentration of Compound No. 11 (ppm) | | |
|---|---|---|---|
| | 4 | 1 | 0 |
| 500 | 0 (1.7) | 0 (12.7) | 81.3 |
| 250 | 0 (1.8) | 0 (13.2) | 84.4 |
| 125 | 0 (1.8) | 0 (13.2) | 84.4 |
| 0 | 2.1 | 15.6 | — |

TABLE 2-21

| Concentration of fluazinam (ppm) | Concentration of Compound No. 4 (ppm) | | |
|---|---|---|---|
| | 4 | 2 | 0 |
| 500 | 0 (0.08) | 0 (0.10) | 2.0 |
| 250 | 0 (0.16) | 0 (0.20) | 4.0 |
| 125 | 0 (0.70) | 0 (0.88) | 17.5 |
| 0 | 4.0 | 5.0 | — |

TABLE 2-22

| Concentration of fluazinam (ppm) | Concentration of Compound No. 5 (ppm) | | | |
|---|---|---|---|---|
| | 4 | 2 | 1 | 0 |
| 500 | 0 (0.02) | 0 (0.08) | 0 (0.25) | 2.0 |
| 250 | 0 (0.04) | 0 (0.16) | 0 (0.50) | 4.0 |
| 0 | 1.0 | 4.0 | 12.5 | — |

TABLE 2-23

| Concentration of fluazinam (ppm) | Concentration of Compound No. 8 (ppm) | | | |
|---|---|---|---|---|
| | 16 | 8 | 4 | 0 |
| 500 | 0 (0.11) | 0 (0.13) | 0 (0.20) | 2.0 |
| 250 | 0 (0.22) | 0 (0.26) | 0 (0.40) | 4.0 |
| 0 | 5.5 | 6.5 | 10.0 | — |

TABLE 2-24

| Concentration of fluazinam (ppm) | Concentration of Compound No. 11 (ppm) | | | |
|---|---|---|---|---|
| | 4 | 2 | 1 | 0 |
| 250 | 0 (0.04) | 0 (0.16) | 0 (0.30) | 4.0 |
| 125 | 0 (0.18) | 0 (0.70) | 0 (1.3) | 17.5 |
| 0 | 1.0 | 4.0 | 7.5 | — |

TABLE 2-25

| Concentration of mancozeb (ppm) | Concentration of Compound No. 4 (ppm) | | | |
|---|---|---|---|---|
| | 4 | 2 | 1 | 0 |
| 500 | 0 (0.78) | 0 (1.3) | 0 (2.4) | 15.6 |
| 0 | 5.0 | 8.1 | 15.6 | — |

TABLE 2-26

| Concentration of mancozeb | Concentration of Compound No. 5 (ppm) | | |
|---|---|---|---|
| (ppm) | 4 | 2 | 0 |
| 125 | 1.3 (1.9) | 2.5 (2.5) | 50.0 |
| 0 | 3.8 | 5.0 | — |

TABLE 2-27

| Concentration of mancozeb | Concentration of Compound No. 7 (ppm) | | | |
|---|---|---|---|---|
| (ppm) | 4 | 2 | 1 | 0 |
| 500 | 12.5 (17.6) | 18.8 (23.5) | 18.8 (25.4) | 31.3 |
| 0 | 56.3 | 75.0 | 81.3 | — |

TABLE 2-28

| Concentration of mancozeb | Concentration of Compound No. 11 (ppm) | | | |
|---|---|---|---|---|
| (ppm) | 4 | 2 | 1 | 0 |
| 500 | 0 (0.48) | 0 (0.59) | 0 (2.4) | 15.6 |
| 250 | 0 (0.97) | 0 (1.2) | 0 (4.9) | 31.3 |
| 125 | 0 (1.6) | 0 (1.9) | 0 (7.8) | 50.0 |
| 0 | 3.1 | 3.8 | 15.6 | — |

TABLE 2-29

| Concentration of chlorothalonil | Concentration of Compound No. 4 (ppm) | | |
|---|---|---|---|
| (ppm) | 4 | 2 | 0 |
| 4 | 1.0 (1.9) | 3.0 (5.8) | 77.5 |
| 0 | 2.5 | 7.5 | — |

TABLE 2-30

| Concentration of chlorothalonil | Concentration of Compound No. 5 (ppm) | | |
|---|---|---|---|
| (ppm) | 4 | 2 | 0 |
| 8 | 0 (0.23) | 0 (1.4) | 45.0 |
| 0 | 0.5 | 3.0 | — |

TABLE 2-31

| Concentration of chlorothalonil | Concentration of Compound No. 8 (ppm) | |
|---|---|---|
| (ppm) | 8 | 0 |
| 16 | 15.0 (15.0) | 37.5 |
| 8 | 15.0 (18.0) | 45.0 |
| 4 | 20.0 (31.0) | 77.5 |
| 0 | 40.0 | — |

TABLE 2-32

| Concentration of chlorothalonil | Concentration of Compound No. 11 (ppm) | | |
|---|---|---|---|
| (ppm) | 8 | 2 | 0 |
| 8 | 1.0 (2.2) | 1.0 (3.6) | 55.0 |
| 0 | 4.0 | 6.5 | — |

TABLE 2-33

| Concentration of procymidone | Concentration of Compound No. 4 (ppm) | |
|---|---|---|
| (ppm) | 1 | 0 |
| 250 | 10.0 (12.4) | 82.5 |
| 125 | 10.0 (12.8) | 85.0 |
| 0 | 15.0 | — |

TABLE 2-34

| Concentration of procymidone | Concentration of Compound No. 5 (ppm) | | |
|---|---|---|---|
| (ppm) | 8 | 2 | 0 |
| 500 | 0 (1.8) | 1.0 (3.2) | 70.0 |
| 0 | 2.5 | 4.5 | — |

TABLE 2-35

| Concentration of procymidone | Concentration of Compound No. 8 (ppm) | | |
|---|---|---|---|
| (ppm) | 8 | 4 | 0 |
| 125 | 3.0 (4.3) | 10.0 (29.8) | 85.0 |
| 0 | 5.0 | 35.0 | — |

TABLE 2-36

| Concentration of procymidone | Concentration of Compound No. 11 (ppm) | | |
|---|---|---|---|
| (ppm) | 4 | 2 | 0 |
| 500 | 0 (0.35) | 0 (0.35) | 70.0 |
| 250 | 0 (0.41) | 0 (0.41) | 82.5 |
| 125 | 0 (0.43) | 0 (0.43) | 85.0 |
| 0 | 0.5 | 0.5 | — |

TABLE 2-37

| Concentration of iprodione | Concentration of Compound No. 4 (ppm) | | |
|---|---|---|---|
| (ppm) | 4 | 2 | 0 |
| 500 | 0 (0.03) | 0 (0.07) | 45.0 |
| 0 | 1.5 | 3.5 | — |

TABLE 2-38

| Concentration of iprodione | Concentration of Compound No. 5 (ppm) | | |
|---|---|---|---|
| (ppm) | 4 | 1 | 0 |
| 500 | 0 (1.1) | 0 (2.3) | 45.0 |
| 250 | 0 (1.1) | 0 (2.3) | 45.0 |
| 0 | 2.5 | 5.0 | — |

TABLE 2-39

| Concentration of iprodione | Concentration of Compound No. 8 (ppm) | | |
|---|---|---|---|
| (ppm) | 8 | 4 | 0 |
| 500 | 2.0 (2.3) | 3.0 (15.8) | 45.0 |
| 0 | 5.0 | 35.0 | — |

TABLE 2-40

| Concentration of iprodione | Concentration of Compound No. 11 (ppm) | | |
|---|---|---|---|
| (ppm) | 4 | 2 | 0 |
| 500 | 0 (0.23) | 0 (0.23) | 45.0 |
| 250 | 0 (0.23) | 0 (0.23) | 45.0 |
| 125 | 0 (0.30) | 0 (0.30) | 60.0 |
| 0 | 0.5 | 0.5 | — |

TABLE 2-41

| Concentration of cymoxanil | Concentration of Compound No. 4 (ppm) | | | |
|---|---|---|---|---|
| (ppm) | 4 | 2 | 1 | 0 |
| 500 | 0 (0.47) | 0 (0.76) | 0 (1.5) | 9.4 |
| 250 | 0 (1.3) | 0 (2.0) | 0 (3.9) | 25.0 |
| 125 | 0 (3.1) | 0 (5.1) | 0 (9.8) | 62.5 |
| 0 | 5.0 | 8.1 | 15.6 | — |

TABLE 2-42

| Concentration of cymoxanil | Concentration of Compound No. 5 (ppm) | | |
|---|---|---|---|
| (ppm) | 2 | 1 | 0 |
| 125 | 0 (3.3) | 0 (9.8) | 62.5 |
| 0 | 5.0 | 15.63 | — |

TABLE 2-43

| Concentration of cymoxanil | Concentration of Compound No. 8 (ppm) | | | |
|---|---|---|---|---|
| (ppm) | 4 | 2 | 1 | 0 |
| 500 | 0 (5.3) | 0 (7.0) | 3.8 (7.6) | 9.4 |
| 250 | 0 (14.1) | 3.8 (18.8) | 6.3 (20.3) | 25.0 |
| 125 | 0 (35.2) | 3.8 (46.9) | 18.8 (50.8) | 62.5 |
| 0 | 56.3 | 75.0 | 81.3 | — |

TABLE 2-44

| Concentration of cymoxanil | Concentration of Compound No. 11 (ppm) | | | |
|---|---|---|---|---|
| (ppm) | 4 | 2 | 1 | 0 |
| 500 | 0 (0.29) | 0 (0.35) | 0 (1.5) | 9.4 |
| 250 | 0 (0.78) | 0 (0.94) | 0 (3.9) | 25.0 |
| 125 | 0 (2.0) | 0 (2.3) | 0 (9.8) | 62.5 |
| 0 | 3.1 | 3.8 | 15.6 | — |

TABLE 2-45

| Concentration of fenhexamid | Concentration of Compound No. 4 (ppm) | | |
|---|---|---|---|
| (ppm) | 4 | 2 | 0 |
| 500 | 0 (0.03) | 0 (0.07) | 50.0 |
| 125 | 0 (0.26) | 0 (0.61) | 52.5 |
| 0 | 1.5 | 3.5 | — |

TABLE 2-46

| Concentration of fenhexamid | Concentration of Compound No. 5 (ppm) | | | |
|---|---|---|---|---|
| (ppm) | 4 | 2 | 1 | 0 |
| 500 | 0 (1.3) | 0 (2.3) | 0 (2.5) | 50.0 |
| 125 | 0 (1.3) | 0 (2.4) | 1.0 (2.6) | 52.5 |
| 0 | 2.5 | 4.5 | 5.0 | — |

TABLE 2-47

| Concentration of fenhexamid | Concentration of Compound No. 8 (ppm) | | |
|---|---|---|---|
| (ppm) | 16 | 8 | 0 |
| 250 | 0 (2.1) | 0 (2.6) | 52.5 |
| 0 | 4.0 | 5.0 | — |

TABLE 2-48

| Concentration of fenhexamid | Concentration of Compound No. 11 (ppm) | | |
|---|---|---|---|
| (ppm) | 4 | 1 | 0 |
| 250 | 0 (0.26) | 0 (2.1) | 52.5 |
| 125 | 0 (0.26) | 1.0 (2.1) | 52.5 |
| 0 | 0.5 | 4.0 | — |

TABLE 2-49

| Concentration of copper oxychloride | Concentration of Compound No. 4 (ppm) | |
|---|---|---|
| (ppm) | 4 | 0 |
| 1000 | 0 (0.39) | 20.7 |
| 500 | 0 (0.42) | 21.9 |
| 250 | 0 (0.48) | 25.0 |
| 0 | 1.9 | — |

TABLE 2-50

| Concentration of copper oxychloride (ppm) | Concentration of Compound No. 5 (ppm) | | |
|---|---|---|---|
| | 2 | 1 | 0 |
| 1000 | 0 (0.39) | 0 (3.2) | 20.6 |
| 250 | 0 (0.48) | 0 (3.9) | 25.0 |
| 0 | 1.9 | 15.6 | — |

TABLE 2-51

| Concentration of copper oxychloride (ppm) | Concentration of Compound No. 8 (ppm) | |
|---|---|---|
| | 16 | 0 |
| 1000 | 0 (0.64) | 20.6 |
| 500 | 0 (0.68) | 21.9 |
| 0 | 3.1 | — |

TABLE 2-52

| Concentration of copper oxychloride (ppm) | Concentration of Compound No. 11 (ppm) | |
|---|---|---|
| | 4 | 0 |
| 1000 | 0 (0.12) | 20.6 |
| 500 | 0 (0.13) | 21.9 |
| 250 | 0 (0.15) | 25.0 |
| 0 | 0.6 | — |

TABLE 2-53

| Concentration of thiophanate-methyl (ppm) | Concentration of Compound No. 5 (ppm) | | | |
|---|---|---|---|---|
| | 4 | 2 | 1 | 0 |
| 125 | 23.0 (26.0) | 25.0 (32.5) | 50.0 (58.5) | 65.0 |
| 63 | 25.0 (30.0) | 30.0 (37.5) | 60.0 (67.5) | 75.0 |
| 0 | 40.0 | 50.0 | 90.0 | — |

TABLE 2-54

| Concentration of thiophanate-methyl (ppm) | Concentration of Compound No. 11 (ppm) | |
|---|---|---|
| | 2 | 0 |
| 125 | 8.0 (13.0) | 65.0 |
| 63 | 12.0 (15.0) | 75.0 |
| 0 | 20.0 | — |

TABLE 2-55

| Concentration of polyoxins (ppm) | Concentration of Compound No. 4 (ppm) | |
|---|---|---|
| | 4 | 0 |
| 250 | 0 (7.0) | 35.0 |
| 125 | 5.0 (8.0) | 40.0 |
| 0 | 20.0 | — |

TABLE 2-56

| Concentration of polyoxins (ppm) | Concentration of Compound No. 5 (ppm) | | | |
|---|---|---|---|---|
| | 4 | 2 | 1 | 0 |
| 250 | 7.0 (14.0) | 15.0 (17.5) | 30.0 (31.5) | 35.0 |
| 0 | 40.0 | 50.0 | 90.0 | — |

TABLE 2-57

| Concentration of polyoxins (ppm) | Concentration of Compound No. 8 (ppm) | | |
|---|---|---|---|
| | 16 | 8 | 0 |
| 250 | 8.0 (10.5) | 10.0 (14.0) | 35.0 |
| 0 | 30.0 | 40.0 | — |

TABLE 2-58

| Concentration of iminoctadine (ppm) | Concentration of Compound No. 4 (ppm) | | | |
|---|---|---|---|---|
| | 4 | 2 | 1 | 0 |
| 16 | 0 (6.0) | 3.0 (7.5) | 10.0 (13.5) | 30.0 |
| 8 | 0 (9.0) | 5.0 (11.3) | 18.0 (20.3) | 45.0 |
| 4 | 0 (13.0) | 8.0 (16.3) | 20.0 (29.3) | 65.0 |
| 0 | 20.0 | 25.0 | 45.0 | — |

TABLE 2-59

| Concentration of iminoctadine (ppm) | Concentration of Compound No. 5 (ppm) | | | |
|---|---|---|---|---|
| | 4 | 2 | 1 | 0 |
| 16 | 8.0 (12.0) | 10.0 (15.0) | 10.0 (27.0) | 30.0 |
| 8 | 12.0 (18.0) | 15.0 (22.0) | 30.0 (40.5) | 45.0 |
| 0 | 40.0 | 50.0 | 90.0 | — |

TABLE 2-60

| Concentration of iminoctadine (ppm) | Concentration of Compound No. 8 (ppm) | | | |
|---|---|---|---|---|
| | 16 | 8 | 4 | 0 |
| 16 | 1.0 (9.0) | 4.0 (12.0) | 4.0 (13.5) | 30.0 |
| 8 | 3.0 (13.5) | 5.0 (18.0) | 5.0 (20.3) | 45.0 |
| 0 | 30.0 | 40.0 | 45.0 | — |

TABLE 2-61

| Concentration of iminoctadine (ppm) | Concentration of Compound No. 4 (ppm) | | | |
|---|---|---|---|---|
| | 4 | 2 | 1 | 0 |
| 16 | 0 (3.0) | 1.0 (6.0) | 2.0 (7.5) | 30.0 |
| 8 | 0 (4.5) | 7.0 (9.0) | 8.0 (11.3) | 45.0 |
| 4 | 0 (6.5) | 9.0 (13.0) | 10.0 (16.3) | 65.0 |
| 0 | 10.0 | 20.0 | 25.0 | — |

TABLE 2-62

| Concentration of triflumizole | Concentration of Compound No. 2 (ppm) | | | |
|---|---|---|---|---|
| (ppm) | 8 | 4 | 2 | 0 |
| 12 | 14 (15.8) | 20 (35) | 25 (49) | 70 |
| 3 | 15 (19.1) | 30 (42.5) | 40 (59.5) | 85 |
| 0 | 22.5 | 50.0 | 70.0 | — |

TABLE 2-63

| Concentration of triflumizole | Concentration of Compound No. 4 (ppm) | | | |
|---|---|---|---|---|
| (ppm) | 4 | 2 | 1 | 0 |
| 12 | 5.0 (5.3) | 0 (10.5) | 0 (35.0) | 70.0 |
| 3 | 0 (6.4) | 0 (12.8) | 10.0 (42.5) | 85.0 |
| 0 | 7.5 | 15.0 | 50.0 | — |

TABLE 2-64

| Concentration of triflumizole | Concentration of Compound No. 5 (ppm) | | | |
|---|---|---|---|---|
| (ppm) | 4 | 2 | 1 | 0 |
| 12 | 0 (1.1) | 0 (21.0) | 4.0 (45.5) | 70.0 |
| 3 | 0 (1.3) | 4.0 (25.5) | 5.0 (55.3) | 85.0 |
| 0 | 1.5 | 30.0 | 65.0 | — |

TABLE 2-65

| Concentration of triflumizole | Concentration of Compound No. 8 (ppm) | | |
|---|---|---|---|
| (ppm) | 8 | 4 | 0 |
| 12 | 6 (7.0) | 10 (24.5) | 70.0 |
| 3 | 7 (8.5) | 27 (29.8) | 85.0 |
| 0 | 10.0 | 35.0 | — |

TABLE 2-66

| Concentration of triflumizole | Concentration of Compound No. 11 (ppm) | | | |
|---|---|---|---|---|
| (ppm) | 4 | 2 | 1 | 0 |
| 12 | 0 (4.6) | 1.0 (5.3) | 1.0 (21.0) | 70.0 |
| 3 | 0 (5.5) | 1.0 (6.4) | 3 (25.5) | 85.0 |
| 0 | 6.5 | 7.5 | 30.0 | — |

TABLE 2-67

| Concentration of hexaconazole | Concentration of Compound No. 2 (ppm) | | |
|---|---|---|---|
| (ppm) | 8 | 4 | 0 |
| 8 | 0 (7.5) | 0 (24.4) | 75.0 |
| 4 | 0 (8.5) | 5.0 (27.6) | 85.0 |
| 2 | 0 (9.5) | 25.0 (30.9) | 95.0 |
| 0 | 10.0 | 32.5 | — |

TABLE 2-68

| Concentration of hexaconazole | Concentration of Compound No. 4 (ppm) | | | |
|---|---|---|---|---|
| (ppm) | 4 | 2 | 1 | 0 |
| 8 | 0 (1.9) | 0 (18.8) | 0 (45.0) | 75.0 |
| 4 | 0 (2.1) | 0 (21.3) | 5.0 (51.0) | 85.0 |
| 2 | 0 (2.4) | 0 (23.8) | 5.0 (57.0) | 95.0 |
| 0 | 2.5 | 25.0 | 60.0 | — |

TABLE 2-69

| Concentration of hexaconazole | Concentration of Compound No. 5 (ppm) | | | |
|---|---|---|---|---|
| (ppm) | 4 | 2 | 1 | 0 |
| 8 | 0 (3.8) | 0 (5.6) | 0 (16.9) | 75.0 |
| 4 | 0 (4.3) | 0 (6.4) | 0 (19.1) | 85.0 |
| 2 | 0 (4.8) | 0 (7.1) | 0 (21.4) | 95.0 |
| 0 | 5.0 | 7.5 | 22.5 | — |

TABLE 2-70

| Concentration of hexaconazole | Concentration of Compound No. 8 (ppm) | | |
|---|---|---|---|
| (ppm) | 16 | 8 | 0 |
| 8 | 0 (1.9) | 0 (6.8) | 75.0 |
| 4 | 0 (2.1) | 0 (7.7) | 85.0 |
| 2 | 0 (2.4) | 0 (8.6) | 95.0 |
| 0 | 2.5 | 9.0 | — |

TABLE 2-71

| Concentration of hexaconazole | Concentration of Compound No. 11 (ppm) | | | |
|---|---|---|---|---|
| (ppm) | 4 | 2 | 1 | 0 |
| 8 | 0 (1.9) | 0 (7.5) | 0 (41.3) | 75.0 |
| 4 | 0 (2.1) | 0 (8.5) | 0 (46.8) | 85.0 |
| 2 | 0 (2.4) | 0 (9.5) | 5.0 (52.3) | 95.0 |
| 0 | 2.5 | 10.0 | 55.0 | — |

TABLE 2-72

| Concentration of hymexazol | Concentration of Compound No. 4 (ppm) | | | |
|---|---|---|---|---|
| (ppm) | 4 | 2 | 1 | 0 |
| 100 | 25.0 (38.0) | 30.0 (42.8) | 30.0 (71.3) | 95.0 |
| 0 | 40.0 | 45.0 | 75.0 | — |

TABLE 2-73

| Concentration of hymexazol | Concentration of Compound No. 5 (ppm) | | | |
|---|---|---|---|---|
| (ppm) | 4 | 2 | 1 | 0 |
| 100 | 15.0 (23.8) | 25.0 (61.8) | 30.0 (76.0) | 95.0 |
| 0 | 25.0 | 65.0 | 80.0 | — |

TABLE 2-74

| Concentration of hymexazol (ppm) | Concentration of Compound No. 8 (ppm) | | |
|---|---|---|---|
| | 8 | 4 | 0 |
| 100 | 50.0 (52.3) | 60.0 (66.5) | 95.0 |
| 0 | 55.0 | 70.0 | — |

TABLE 2-75

| Concentration of hymexazol (ppm) | Concentration of Compound No. 11 (ppm) | |
|---|---|---|
| | 4 | 0 |
| 100 | 0 (6.2) | 95.0 |
| 0 | 6.5 | — |

TABLE 2-76

| Concentration of pyrimethanil (ppm) | Concentration of Compound No. 4 (ppm) | | |
|---|---|---|---|
| | 4 | 1 | 0 |
| 25 | 15.0 (36.0) | 60.0 (67.5) | 90.0 |
| 0 | 40.0 | 75.0 | — |

TABLE 2-77

| Concentration of pyrimethanil (ppm) | Concentration of Compound No. 5 (ppm) | |
|---|---|---|
| | 1 | 0 |
| 25 | 50.0 (72.0) | 90.0 |
| 0 | 80.0 | — |

TABLE 2-78

| Concentration of pyrimethanil (ppm) | Concentration of Compound No. 8 (ppm) | | | |
|---|---|---|---|---|
| | 16 | 8 | 4 | 0 |
| 25 | 10.0 (15.8) | 40.0 (49.5) | 60.0 (63.0) | 90.0 |
| 0 | 17.5 | 55.0 | 70.0 | — |

TABLE 2-79

| Concentration of pyrimethanil (ppm) | Concentration of Compound No. 11 (ppm) | | | |
|---|---|---|---|---|
| | 4 | 2 | 1 | 0 |
| 25 | 0 (5.9) | 3.0 (13.5) | 20.0 (40.5) | 90.0 |
| 0 | 6.5 | 15.0 | 45.0 | — |

TABLE 2-80

| Concentration of trifloxystrobin (ppm) | Concentration of Compound No. 2 (ppm) | | | |
|---|---|---|---|---|
| | 8 | 4 | 2 | 0 |
| 200 | 0 (11.3) | 3.0 (25.0) | 15.0 (35.0) | 50.0 |
| 4 | 5.0 (19.1) | 20.0 (42.5) | 30.0 (59.5) | 85.0 |
| 0 | 22.5 | 50.0 | 70.0 | — |

TABLE 2-81

| Concentration of trifloxystrobin (ppm) | Concentration of Compound No. 4 (ppm) | | | |
|---|---|---|---|---|
| | 4 | 2 | 1 | 0 |
| 200 | 0 (3.8) | 0 (7.5) | 20.0 (25.0) | 50.0 |
| 4 | 0 (6.4) | 1.0 (12.8) | 21.0 (42.5) | 85.0 |
| 0 | 7.5 | 15.0 | 50.0 | — |

TABLE 2-82

| Concentration of trifloxystrobin (ppm) | Concentration of Compound No. 5 (ppm) | | | |
|---|---|---|---|---|
| | 4 | 2 | 1 | 0 |
| 200 | 0 (0.75) | 1.0 (15.0) | 20.0 (32.5) | 50.0 |
| 4 | 0 (1.3) | 10.0 (25.5) | 20.0 (55.3) | 85.0 |
| 0 | 1.5 | 30.0 | 65.0 | — |

TABLE 2-83

| Concentration of trifloxystrobin (ppm) | Concentration of Compound No. 8 (ppm) | | |
|---|---|---|---|
| | 2 | 1 | 0 |
| 4 | 7.0 (8.5) | 27.0 (29.8) | 85.0 |
| 0 | 10.0 | 35.0 | — |

TABLE 2-84

| Concentration of trifloxystrobin (ppm) | Concentration of Compound No. 11 (ppm) | | | |
|---|---|---|---|---|
| | 4 | 2 | 1 | 0 |
| 200 | 0 (3.3) | 3.0 (3.8) | 5.0 (15.0) | 50.0 |
| 4 | 0 (5.5) | 3.0 (6.4) | 20.0 (25.5) | 85.0 |
| 0 | 6.5 | 7.5 | 30.0 | — |

TABLE 2-85

| Concentration of pyraclostrobin (ppm) | Concentration of Compound No. 4 (ppm) | |
|---|---|---|
| | 1 | 0 |
| 100 | 70.0 (75.0) | 100 |
| 0 | 75.0 | — |

TABLE 2-86

| Concentration of pyraclostrobin | Concentration of Compound No. 5 (ppm) | | | |
|---|---|---|---|---|
| (ppm) | 4 | 2 | 1 | 0 |
| 100 | 10.0 (25.0) | 50.0 (65.0) | 50.0 (80.0) | 100 |
| 0 | 25.0 | 65.0 | 80.0 | — |

TABLE 2-87

| Concentration of pyraclostrobin | Concentration of Compound No. 11 (ppm) | |
|---|---|---|
| (ppm) | 1 | 0 |
| 100 | 5.0 (45.0) | 100 |
| 0 | 45.0 | — |

TABLE 2-88

| Concentration of potassium bicarbonate | Concentration of Compound No. 2 (ppm) | |
|---|---|---|
| (ppm) | 2 | 0 |
| 1000 | 0 (2.0) | 20.0 |
| 0 | 10.0 | — |

TABLE 2-89

| Concentration of potassium bicarbonate | Concentration of Compound No. 4 (ppm) | |
|---|---|---|
| (ppm) | 2 | 0 |
| 1000 | 0 (1.5) | 20.0 |
| 100 | 0 (1.9) | 25.0 |
| 0 | 7.5 | — |

TABLE 2-90

| Concentration of potassium bicarbonate | Concentration of Compound No. 5 (ppm) | |
|---|---|---|
| (ppm) | 2 | 0 |
| 100 | 0 (0.63) | 25.0 |
| 0 | 2.5 | — |

TABLE 2-91

| Concentration of potassium bicarbonate | Concentration of Compound No. 8 (ppm) | |
|---|---|---|
| (ppm) | 16 | 0 |
| 100 | 0 (1.6) | 25.0 |
| 0 | 6.5 | — |

TABLE 2-92

| Concentration of potassium bicarbonate | Concentration of Compound No. 11 (ppm) | | | |
|---|---|---|---|---|
| (ppm) | 4 | 2 | 1 | 0 |
| 100 | 0 (2.5) | 0 (3.1) | 5.0 (5.6) | 25.0 |
| 0 | 10.0 | 12.5 | 22.5 | — |

TABLE 2-93

| Concentration of meptyldinocap | Concentration of Compound No. 2 (ppm) | | | |
|---|---|---|---|---|
| (ppm) | 8 | 4 | 2 | 0 |
| 3 | 0 (0.40) | 0 (0.29) | 0 (0.25) | 2.5 |
| 0 | 16.0 | 11.5 | 10.0 | — |

TABLE 2-94

| Concentration of meptyldinocap | Concentration of Compound No. 4 (ppm) | | |
|---|---|---|---|
| (ppm) | 2 | 1 | 0 |
| 3 | 0 (0.19) | 0 (0.13) | 2.5 |
| 0 | 7.5 | 5.0 | — |

TABLE 2-95

| Concentration of meptyldinocap | Concentration of Compound No. 5 (ppm) | | |
|---|---|---|---|
| (ppm) | 4 | 1 | 0 |
| 3 | 0 (0.06) | 0 (0.25) | 2.5 |
| 0 | 2.5 | 10.0 | — |

TABLE 2-96

| Concentration of meptyldinocap | Concentration of Compound No. 8 (ppm) | |
|---|---|---|
| (ppm) | 8 | 0 |
| 3 | 0 (0.19) | 2.5 |
| 0 | 7.5 | — |

TABLE 2-97

| Concentration of meptyldinocap | Concentration of Compound No. 11 (ppm) | | |
|---|---|---|---|
| (ppm) | 4 | 1 | 0 |
| 3 | 0 (0.25) | 0 (0.56) | 2.5 |
| 0 | 10.0 | 22.5 | — |

TABLE 2-98

| Concentration of dimethomorph (ppm) | Concentration of Compound No. 5 (ppm) | | |
|---|---|---|---|
| | 2 | 1 | 0 |
| 500 | 50.0 (61.8) | 70.0 (76.0) | 95.0 |
| 0 | 65.0 | 80.0 | — |

TABLE 2-99

| Concentration of potassium phosphite (ppm) | Concentration of Compound No. 2 (ppm) | | | |
|---|---|---|---|---|
| | 8 | 4 | 2 | 0 |
| 500 | 15.0 (18.0) | 20.0 (40.0) | 30.0 (56.0) | 80.0 |
| 0 | 22.5 | 50.0 | 70.0 | — |

TABLE 2-100

| Concentration of potassium phosphite (ppm) | Concentration of Compound No. 4 (ppm) | | | |
|---|---|---|---|---|
| | 4 | 2 | 1 | 0 |
| 500 | 0 (6.0) | 4.0 (12.0) | 30.0 (40.0) | 80.0 |
| 100 | 0 (6.4) | 5.0 (12.8) | 40.0 (42.5) | 85.0 |
| 0 | 7.5 | 15.0 | 50.0 | — |

TABLE 2-101

| Concentration of potassium phosphite (ppm) | Concentration of Compound No. 5 (ppm) | | |
|---|---|---|---|
| | 2 | 1 | 0 |
| 500 | 14.0 (24.0) | 30.0 (52.0) | 80.0 |
| 100 | 15.0 (25.5) | 40.0 (55.3) | 85.0 |
| 0 | 30.0 | 65.0 | — |

TABLE 2-102

| Concentration of potassium phosphite (ppm) | Concentration of Compound No. 8 (ppm) | |
|---|---|---|
| | 4 | 0 |
| 500 | 7.0 (8.0) | 80.0 |
| 100 | 8.0 (8.5) | 85.0 |
| 0 | 10.0 | — |

TABLE 2-103

| Concentration of potassium phosphite (ppm) | Concentration of Compound No. 11 (ppm) | |
|---|---|---|
| | 4 | 0 |
| 500 | 0 (5.2) | 80.0 |
| 100 | 5.0 (5.5) | 85.0 |
| 0 | 6.5 | — |

TABLE 2-104

| Concentration of tolclofosmethyl (ppm) | Concentration of Compound No. 4 (ppm) | | | |
|---|---|---|---|---|
| | 4 | 2 | 1 | 0 |
| 100 | 10.0 (32.0) | 15.0 (36.0) | 20.0 (60.0) | 80.0 |
| 0 | 40.0 | 45.0 | 75.0 | — |

TABLE 2-105

| Concentration of tolclofosmethyl (ppm) | Concentration of Compound No. 5 (ppm) | | | |
|---|---|---|---|---|
| | 4 | 2 | 1 | 0 |
| 100 | 0 (20.0) | 5.0 (52.0) | 30.0 (64.0) | 80.0 |
| 0 | 25.0 | 65.0 | 80.0 | — |

TABLE 2-106

| Concentration of tolclofosmethyl (ppm) | Concentration of Compound No. 8 (ppm) | | | |
|---|---|---|---|---|
| | 16 | 8 | 4 | 0 |
| 100 | 0 (14.0) | 10.0 (44.0) | 30.0 (56.0) | 80.0 |
| 0 | 17.5 | 55.0 | 70.0 | — |

TABLE 2-107

| Concentration of tolclofosmethyl (ppm) | Concentration of Compound No. 11 (ppm) | | | |
|---|---|---|---|---|
| | 4 | 2 | 1 | 0 |
| 100 | 0 (5.2) | 5.0 (12.0) | 10.0 (36.0) | 80.0 |
| 0 | 6.5 | 15.0 | 45.0 | — |

TABLE 2-108

| Concentration of propamocarb hydrochloride (ppm) | Concentration of Compound No. 2 (ppm) | | |
|---|---|---|---|
| | 8 | 4 | 0 |
| 100 | 0 (9.5) | 0 (30.9) | 95.0 |
| 10 | 0 (9.5) | 10.0 (30.9) | 95.0 |
| 0 | 10.0 | 32.5 | — |

TABLE 2-109

| Concentration of propamocarb hydrochloride (ppm) | Concentration of Compound No. 4 (ppm) | | |
|---|---|---|---|
| | 4 | 2 | 0 |
| 1000 | 0 (2.3) | 5.0 (23.1) | 92.5 |
| 100 | 0 (2.4) | 10.0 (23.8) | 95.0 |
| 10 | 0 (2.4) | 10.0 (23.8) | 95.0 |
| 0 | 2.5 | 25.0 | — |

TABLE 2-110

| Concentration of propamocarb hydrochloride | Concentration of Compound No. 5 (ppm) | | |
|---|---|---|---|
| (ppm) | 4 | 2 | 0 |
| 1000 | 0 (4.6) | 0 (6.9) | 92.5 |
| 100 | 0 (4.8) | 0 (7.1) | 95.0 |
| 10 | 0 (4.8) | 0 (7.1) | 95.0 |
| 0 | 5.0 | 7.5 | — |

TABLE 2-111

| Concentration of propamocarb hydrochloride | Concentration of Compound No. 8 (ppm) | | |
|---|---|---|---|
| (ppm) | 16 | 4 | 0 |
| 1000 | 0 (2.3) | 2.0 (11.6) | 92.5 |
| 100 | 0 (2.4) | 5.0 (11.9) | 95.0 |
| 10 | 2.0 (2.4) | 5.0 (11.9) | 95.0 |
| 0 | 2.5 | 12.5 | — |

TABLE 2-112

| Concentration of propamocarb hydrochloride | Concentration of Compound No. 11 (ppm) | | | |
|---|---|---|---|---|
| (ppm) | 4 | 2 | 1 | 0 |
| 1000 | 0 (2.3) | 0 (9.3) | 5.0 (50.9) | 92.5 |
| 100 | 0 (2.4) | 0 (9.5) | 10.0 (52.3) | 95.0 |
| 10 | 0 (2.4) | 0 (9.5) | 10.0 (52.3) | 95.0 |
| 0 | 2.5 | 10.0 | 55.0 | — |

TEST EXAMPLE 3

Test on Preventive Effect Against Wheat Glum Bloth

Wheat (cultivar: Norin-61-go) was cultivated in a plastic pot having a diameter of 7.5 cm, and when it reached 1.5-leaf stage, a mixed chemical solution having the respective sample compounds adjusted to prescribed concentrations, was applied by a spray gun in an amount of 10 ml per seedling. After the chemical solution dried, a suspension of conidia of *Septoria nodorum* was sprayed and inoculated and maintained at 20° C. for 7 days (for the first 3 days maintained under high humidity condition). Thereafter, the area of lesions was investigated, and the diseased area ratio to non-treated section was obtained by the following equation. The results are shown in Tables 3-1 to 3-14.

Diseased area ratio to non-treated section = $(a/b) \times 100$ a: Average area of lesions in treated section b: Average area of lesions in non-treated section Further, the theoretical value was calculated by a Colby's formula and shown in brackets ( ) in Tables 3-1 to 3-14. Since the diseased area ratio to non-treated section (experimental value) is lower than the theoretical value, the composition of the present invention can be said to have a synergistic effect.

TABLE 3-1

| Concentration of myclobutanil | Concentration of Compound No. 2 (ppm) | | |
|---|---|---|---|
| (ppm) | 50 | 12.5 | 0 |
| 20 | 0 (12.3) | 5.0 (17.5) | 35.0 |
| 5 | 7.0 (21.0) | 10.0 (30.0) | 60.0 |
| 0 | 35.0 | 50.0 | — |

TABLE 3-2

| Concentration of myclobutanil | Concentration of Compound No. 4 (ppm) | | |
|---|---|---|---|
| (ppm) | 50 | 12.5 | 0 |
| 20 | 0 (7.0) | 7.0 (12.3) | 35.0 |
| 5 | 7.0 (12.0) | 7.0 (21.0) | 60.0 |
| 0 | 20.0 | 35.0 | — |

TABLE 3-3

| Concentration of myclobutanil | Concentration of Compound No. 5 (ppm) | | |
|---|---|---|---|
| (ppm) | 50 | 12.5 | 0 |
| 20 | 5.0 (7.0) | 7.0 (10.5) | 35.0 |
| 0 | 20.0 | 30.0 | — |

TABLE 3-4

| Concentration of myclobutanil | Concentration of Compound No. 8 (ppm) | | |
|---|---|---|---|
| (ppm) | 50 | 12.5 | 0 |
| 20 | 0 (7.0) | 2.0 (12.3) | 35.0 |
| 5 | 2.0 (12.0) | 8.0 (21.0) | 60.0 |
| 0 | 20.0 | 35.0 | — |

TABLE 3-5

| Concentration of myclobutanil | Concentration of Compound No. 11 (ppm) | | |
|---|---|---|---|
| (ppm) | 50 | 12.5 | 0 |
| 20 | 2.0 (8.8) | 5.0 (17.5) | 35.0 |
| 5 | 3.0 (15.0) | 10.0 (30.0) | 60.0 |
| 0 | 25.0 | 50.0 | — |

TABLE 3-6

| Concentration of prochloraz | Concentration of Compound No. 4 (ppm) | | |
|---|---|---|---|
| (ppm) | 50 | 12.5 | 0 |
| 20 | 0 (3.0) | 0 (5.3) | 15.0 |
| 5 | 0 (8.0) | 0 (14.0) | 40.0 |
| 0 | 20.0 | 35.0 | — |

TABLE 3-7

| Concentration of prochloraz (ppm) | Concentration of Compound No. 5 (ppm) | | |
|---|---|---|---|
| | 50 | 12.5 | 0 |
| 20 | 0 (3.0) | 0 (4.5) | 15.0 |
| 5 | 5.0 (8.0) | 10.0 (12.0) | 40.0 |
| 0 | 20.0 | 30.0 | — |

TABLE 3-8

| Concentration of prochloraz (ppm) | Concentration of Compound No. 8 (ppm) | | |
|---|---|---|---|
| | 50 | 12.5 | 0 |
| 20 | 0 (3.0) | 2.0 (5.3) | 15.0 |
| 5 | 7.0 (8.0) | 13.0 (14.0) | 40.0 |
| 0 | 20.0 | 35.0 | — |

TABLE 3-9

| Concentration of prochloraz (ppm) | Concentration of Compound No. 11 (ppm) | | |
|---|---|---|---|
| | 50 | 12.5 | 0 |
| 20 | 0 (3.8) | 7.0 (7.5) | 15.0 |
| 5 | 3.0 (10.0) | 15.0 (20.0) | 40.0 |
| 0 | 25.0 | 50.0 | — |

TABLE 3-10

| Concentration of prothioconazole (ppm) | Concentration of Compound No. 2 (ppm) | | |
|---|---|---|---|
| | 50 | 12.5 | 0 |
| 10 | 0 (10.5) | 0 (15.0) | 30.0 |
| 2.5 | 9.0 (14.0) | 10.0 (20.0) | 40.0 |
| 0 | 35.0 | 50.0 | — |

TABLE 3-11

| Concentration of prothioconazole (ppm) | Concentration of Compound No. 4 (ppm) | | |
|---|---|---|---|
| | 50 | 12.5 | 0 |
| 10 | 0 (6.0) | 3.0 (10.5) | 30.0 |
| 2.5 | 3.0 (8.0) | 10.0 (14.0) | 40.0 |
| 0 | 20.0 | 35.0 | — |

TABLE 3-12

| Concentration of prothioconazole (ppm) | Concentration of Compound No. 5 (ppm) | | |
|---|---|---|---|
| | 50 | 12.5 | 0 |
| 10 | 0 (6.0) | 7.0 (9.0) | 30.0 |
| 2.5 | 5.0 (8.0) | 10.0 (12.0) | 40.0 |
| 0 | 20.0 | 30.0 | — |

TABLE 3-13

| Concentration of prothioconazole (ppm) | Concentration of Compound No. 8 (ppm) | | |
|---|---|---|---|
| | 50 | 12.5 | 0 |
| 10 | 0 (6.0) | 0 (10.5) | 30.0 |
| 2.5 | 3.0 (8.0) | 13.0 (14.0) | 40.0 |
| 0 | 20.0 | 35.0 | — |

TABLE 3-14

| Concentration of prothioconazole (ppm) | Concentration of Compound No. 11 (ppm) | | |
|---|---|---|---|
| | 50 | 12.5 | 0 |
| 10 | 0 (7.5) | 2.0 (15.0) | 30.0 |
| 2.5 | 0 (10.0) | 2.0 (20.0) | 40.0 |
| 0 | 25.0 | 50.0 | — |

TEST EXAMPLE 4

Test on Preventive Effect Against Kidney Bean Gray Mold

Kidney bean (cultivar: Taisyou Kintoki) was cultivated in a plastic pot having a diameter of 12.0 cm, and when it reached 2.5-leaf stage, a mixed chemical solution having the respective test compounds adjusted to prescribed concentrations, was applied by a spray gun in an amount of 10 ml per seedling. After the chemical solution dried, the leaf was cut out, and a filter paper disk (8 mm in diameter) was placed on the leaf. Then, 120 μl of a suspension of spores of *Botrytis cinerea* ($1.0 \times 10^6$ spores/ml) was dropped thereon and inoculated. The system was maintained under a humidity condition at 20° C. for three days, whereupon the area of lesions was investigated, and the diseased area ratio to non-treated section was obtained in the same manner as in Test Example 3. The results are shown in Tables 4-1 to 4-19. Further, the theoretical value was calculated by a Colby's formula and shown in brackets ( ) in Tables 4-1 to 4-19. Since the diseased area ratio to non-treated section (experimental value) is lower than the theoretical value, the composition of the present invention can be said to have a synergistic effect.

TABLE 4-1

| Concentration of Compound α (ppm) | Concentration of Compound No. 2 (ppm) | |
|---|---|---|
| | 4 | 0 |
| 8 | 0 (9.8) | 15.0 |
| 0 | 65.0 | — |

TABLE 4-2

| Concentration of Compound α (ppm) | Concentration of Compound No. 5 (ppm) | |
|---|---|---|
| | 4 | 0 |
| 8 | 0 (11.1) | 15.0 |
| 0 | 74.0 | — |

TABLE 4-3

| Concentration of Compound α (ppm) | Concentration of Compound No. 8 (ppm) | |
|---|---|---|
| | 4 | 0 |
| 4 | 0 (6.5) | 43.0 |
| 0 | 15.0 | — |

TABLE 4-4

| Concentration of Compound α (ppm) | Concentration of Compound No. 11 (ppm) | |
|---|---|---|
| | 4 | 0 |
| 8 | 0 (10.5) | 15.0 |
| 4 | 22.0 (30.1) | 43.0 |
| 0 | 70.0 | — |

TABLE 4-5

| Concentration of pyribencarb (ppm) | Concentration of Compound No. 2 (ppm) | |
|---|---|---|
| | 4 | 0 |
| 8 | 15.0 (42.3) | 65.0 |
| 4 | 35.0 (45.5) | 70.0 |
| 0 | 65.0 | — |

TABLE 4-6

| Concentration of pyribencarb (ppm) | Concentration of Compound No. 4 (ppm) | |
|---|---|---|
| | 4 | 0 |
| 8 | 0 (45.5) | 65.0 |
| 4 | 35.0 (49.0) | 70.0 |
| 0 | 70.0 | — |

TABLE 4-7

| Concentration of pyribencarb (ppm) | Concentration of Compound No. 5 (ppm) | |
|---|---|---|
| | 4 | 0 |
| 8 | 0 (48.1) | 65.0 |
| 4 | 0 (51.8) | 70.0 |
| 0 | 74.0 | — |

TABLE 4-8

| Concentration of pyribencarb (ppm) | Concentration of Compound No. 8 (ppm) | |
|---|---|---|
| | 4 | 0 |
| 4 | 0 (10.5) | 70.0 |
| 0 | 15.0 | — |

TABLE 4-9

| Concentration of pyribencarb (ppm) | Concentration of Compound No. 11 (ppm) | |
|---|---|---|
| | 4 | 0 |
| 8 | 0 (45.5) | 65.0 |
| 4 | 0 (49.0) | 70.0 |
| 0 | 70.0 | — |

TABLE 4-10

| Concentration of cyflufenamid (ppm) | Concentration of Compound No. 4 (ppm) | |
|---|---|---|
| | 8 | 0 |
| 10 | 38.0 (56.4) | 87.3 |
| 0 | 64.6 | — |

TABLE 4-11

| Concentration of cyflufenamid (ppm) | Concentration of Compound No. 5 (ppm) | | |
|---|---|---|---|
| | 8 | 4 | 0 |
| 100 | 22.8 (61.5) | 48.1 (68.7) | 82.3 |
| 0 | 74.7 | 83.5 | — |

TABLE 4-12

| Concentration of cyflufenamid (ppm) | Concentration of Compound No. 8 (ppm) | |
|---|---|---|
| | 4 | 0 |
| 100 | 75.9 (81.2) | 82.3 |
| 10 | 70.9 (86.2) | 87.3 |
| 0 | 98.7 | — |

TABLE 4-13

| Concentration of proquinazid (ppm) | Concentration of Compound No. 4 (ppm) | |
|---|---|---|
| | 8 | 0 |
| 100 | 55.7 (59.7) | 92.4 |
| 10 | 55.7 (62.2) | 96.2 |
| 0 | 64.6 | — |

TABLE 4-14

| Concentration of proquinazid (ppm) | Concentration of Compound No. 5 (ppm) | | |
|---|---|---|---|
| | 8 | 4 | 0 |
| 100 | 55.7 (69.0) | 43.0 (77.2) | 92.4 |
| 10 | 70.9 (71.9) | 65.8 (80.3) | 96.2 |
| 0 | 74.7 | 83.5 | — |

TABLE 4-15

| Concentration of proquinazid | Concentration of Compound No. 8 (ppm) | |
| --- | --- | --- |
| (ppm) | 4 | 0 |
| 100 | 78.5 (91.2) | 92.4 |
| 0 | 98.7 | — |

TABLE 4-16

| Concentration of proquinazid | Concentration of Compound No. 11 (ppm) | |
| --- | --- | --- |
| (ppm) | 8 | 0 |
| 100 | 40.5 (51.5) | 92.4 |
| 10 | 50.6 (53.6) | 96.2 |
| 0 | 55.7 | — |

TABLE 4-17

| Concentration of compound γ | Concentration of Compound No. 4 (ppm) | |
| --- | --- | --- |
| (ppm) | 4 | 0 |
| 10 | 55.7 (70.6) | 88.6 |
| 1 | 55.7 (70.6) | 88.6 |
| 0 | 79.7 | — |

TABLE 4-18

| Concentration of compound γ | Concentration of Compound No. 5 (ppm) | | |
| --- | --- | --- | --- |
| (ppm) | 8 | 4 | 0 |
| 10 | 35.4 (66.2) | 60.8 (74.0) | 88.6 |
| 0 | 74.7 | 83.5 | — |

TABLE 4-19

| Concentration of compound γ | Concentration of Compound No. 8 (ppm) | |
| --- | --- | --- |
| (ppm) | 4 | 0 |
| 10 | 10.1 (87.5) | 88.6 |
| 1 | 83.5 (87.5) | 88.6 |
| 0 | 98.7 | — |

TEST EXAMPLE 5

Test on Antifungal Activity Against Rice Blast Pathogen

Mycelial growth of *Phyicularia oryzae* preliminarily obtained by cultivation was punched out by a cork borer having a diameter of 4 mm and transplanted on a potato sucrose agar medium containing mixed chemical agents adjusted to prescribed concentrations. The system was left to stand at 25° C. for 3 days for cultivation, and thereafter, the diameter of mycelial growth was measured. The incidence to non-treated section was obtained by the following equation, and the results are shown in Table 5-1 to 5-3.

Incidence to non-treated section = $(a/b) \times 100$ a: Average diameter (mm) of mycelial growth in treated section b: Average diameter (mm) of mycelial growth in non-treated section.

Further, the theoretical value was calculated by a Colby's formula and shown in brackets ( ) in Tables 5-1 to 5-3. Since the incidence to non-treated section is lower than the theoretical value, the composition of the present invention can be said to have a synergistic effect.

TABLE 5-1

| Concentration of ferimzone | Concentration of Compound No. 2 (ppm) | |
| --- | --- | --- |
| (ppm) | 100 | 0 |
| 0.5 | 2.2 (9.0) | 10.9 |
| 0 | 82.6 | — |

TABLE 5-2

| Concentration of ferimzone | Concentration of Compound No. 4 (ppm) | | |
| --- | --- | --- | --- |
| (ppm) | 100 | 10 | 0 |
| 0.5 | 0 (7.6) | 6.5 (7.8) | 10.9 |
| 0.25 | 26.1 (33.3) | 28.3 (34.3) | 47.8 |
| 0 | 69.6 | 71.7 | — |

TABLE 5-3

| Concentration of ferimzone | Concentration of Compound No. 11 (ppm) | | |
| --- | --- | --- | --- |
| (ppm) | 50 | 5 | 0 |
| 0.5 | 0 (6.9) | 0 (8.1) | 10.9 |
| 0.25 | 26.1 (30.1) | 28.3 (35.3) | 47.8 |
| 0 | 63.0 | 73.9 | — |

TEST EXAMPLE 6

Test on Antifungal Activity Against Gray Mold Pathogen

Mycelial growth of *Botrytis cinerea* preliminarily obtained by cultivation was punched out by a cork borer having a diameter of 4 mm and transplanted on a potato sucrose agar medium containing mixed chemical agents adjusted to prescribed concentrations. The system was left to stand at 25° C. for 3 days for cultivation, whereupon the diameter of mycelial growth was measured. The incidence to non-treated section was obtained in the same manner as the above Test Example 5, and the results are shown in Table 6-1 to 6-3.

Further, the theoretical value was calculated by a Colby's formula and shown in brackets ( ) in Tables 6-1 to 6-3. Since the incidence to non-treated section is lower than the theoretical value, the composition of the present invention can be said to have a synergistic effect.

TABLE 6-1

| Concentration of captan (ppm) | Concentration of Compound No. 4 (ppm) | |
|---|---|---|
| | 0.5 | 0 |
| 1 | 41.9 (42.7) | 94.4 |
| 0 | 45.2 | — |

TABLE 6-2

| Concentration of captan (ppm) | Concentration of Compound No. 5 (ppm) | |
|---|---|---|
| | 5 | 0 |
| 1 | 27.4 (30.5) | 94.4 |
| 0 | 32.3 | — |

TABLE 6-3

| Concentration of captan (ppm) | Concentration of Compound No. 11 (ppm) | | |
|---|---|---|---|
| | 50 | 5 | 0 |
| 1 | 22.6 (30.5) | 40.3 (43.4) | 94.4 |
| 0 | 32.3 | 46.0 | — |

TEST EXAMPLE 7

Test on Antifungal Activity Against Gray Mold Pathogen

On a potato sucrose agar medium in a Petri dish, a suspension of spores of *Botrytis cinerea* (spore concentration: $2\times10^6$ spores/ml) was spread in an amount of 300 µl per Petri dish and dried. Thereon, filter paper immersed in a chemical solution (30 ppm) of Compound No. 2 and a filter paper immersed in a chemical solution (30 ppm) of fluazinam were placed to intersect each other (the respective filter papers were air-dried ones of 0.7 cm×8 cm). The system was left to stand at 20° C. for 4 days, and then, mycelial growth of *Botrytis cinerea* was observed (photograph in FIG. 1). In FIG. 1, the transversely-placed filter paper is one immersed in Compound No. 2, and the longitudinally-placed filter paper is one immersed in fluazinam. The white turbid portion is a portion where *Botrytis cinerea* proliferated.

Both end portions of the transversely-placed filter paper are in contact with mycelial growth area of *Botrytis cinerea*, thus indicating that by the single use of Compound No. 2 (30 ppm), no adequate controlling effect can be obtained. Whereas, both end portions of the longitudinally-placed filter paper, are not in contact with mycelial growth area of *Botrytis cinerea*, thus indicating that by the single use of fluazinam (30 ppm), a certain controlling effect is obtained. Whereas, in the vicinity of the intersection of filter papers, the filter papers are not in contact with mycelial growth area of *Botrytis cinerea* over a wide range, thus indicating that when Compound No. 2 and fluazinam are used in combination, an excellent controlling effect can be obtained.

Figure 2:
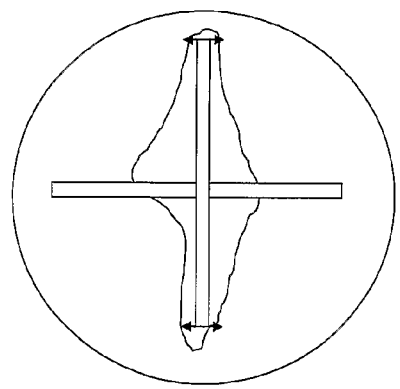
FIG. 2 is a view diagrammatically showing the results of the test on antimicrobial activity against gray mold pathogen in Test Example 7, wherein the four portions at which the distance from both ends of the longitudinally-placed filter paper to mycelial growth area of *Botrytis cinerea* was measured, are shown by arrows.
Figure 3:
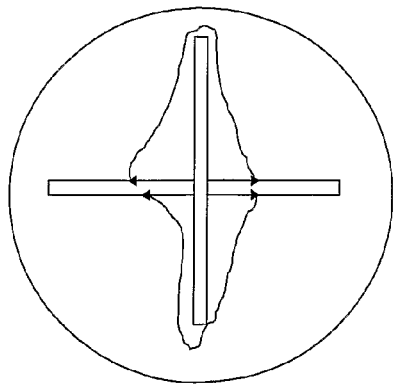
FIG. 3 is a view diagrammatically showing the results of the test on antimicrobial activity against gray mold pathogen in Test Example 7, wherein the four portions at which the distance from the portion where filter papers intersect each other to mycelial growth area of *Botrytis cinerea*, are shown by arrows.

This controlling effect was numerically represented. Namely, the distance from both ends of the longitudinally-placed filter paper corresponding to a single use section of fluazinam to the mycelial growth area of *Botrytis cinerea* was measured at four portions (arrow portions in FIG. 2), and averaged to obtain 5 mm. On the other hand, the distance from the portion where the filter papers intersect each other, corresponding to a mixed use section of Compound No. 2 and fluazinam to mycelial growth area of *Botrytis cinerea* was measured at four portions (arrow portions in FIG. 3) and averaged to obtain 17 mm.

TEST EXAMPLE 8

Test on Antifungal Activity Against Gray Mold Pathogen

The test was carried out in the same manner as in Test Example 7 except that 30 ppm of fluazinam was changed to 30 ppm of oxpoconazole fumarate. As a result, the distance (average value) from both ends of the longitudinally-placed filter paper corresponding to the single use section of oxpoconazole fumarate to mycelial growth area of *Botrytis cinerea*, was 7.5 mm. Whereas, the distance (average value) from the portion where the filter papers intersect each other corresponding to a mixed use section of Compound No. 2 and oxpoconazole fumarate to mycelial growth area of *Botrytis cinerea* was 13.3 mm.

Now, Formulation Examples of the composition of the present invention will be described, but it should be understood that the blend components, blend ratio, type of formulation, etc. in the present invention are not limited to the following examples.

FORMULATION EXAMPLE 1

| | |
|---|---|
| (a) Kaolin | 78 parts by weight |
| (b) Condensate of β-naphthalenesulfonic acid sodium salt with formalin | 2 parts by weight |
| (c) Polyoxyethylene alkylaryl ether sulfate | 5 parts by weight |
| (d) Hydrated amorphous silicon dioxide | 15 parts by weight |

A mixture of the above components, a compound of the formula (I) and epoxiconazole are mixed in a weight ratio of 8:1:1 to obtain a wettable powder.

FORMULATION EXAMPLE 2

| | |
|---|---|
| (a) Compound of the formula (I) | 0.5 part by weight |
| (b) Epoxiconazole | 0.5 part by weight |
| (c) Bentonite | 20 parts by weight |
| (d) Kaolin | 74 parts by weight |
| (e) Sodium lignin sulfonate | 5 parts by weight |

To the above components, a suitable amount of water required for granulation is added, followed by mixing and granulation to obtain granules.

FORMULATION EXAMPLE 3

| | |
|---|---|
| (a) Compound of the formula (I) | 2 parts by weight |
| (b) Epoxiconazole | 3 parts by weight |
| (c) Talc | 95 parts by weight |

The above components are uniformly mixed to obtain a dust.

The entire disclosure of Japanese Patent Application No. 2007-287699 filed on Nov. 5, 2007 including specification, claims, drawings and summary is incorporated herein by reference in its entirety.

The invention claimed is:

1. A fungicidal composition comprising synergistically effective amounts of:
   (a) N-[[2'-methyl-4'-(2-propyloxy)-1,1-dimethyl]phenacyl]-3-methyl-2-thiophenecarboxamide as a carboxylic acid amide derivative; and
   (b) at least one fungicidal compound selected from the group consisting of ferimzone, 5-chloro-7-(4-methylpiperidin-1-yl)-6-(2,4,6-trifluorophenyl)-[1,2,4]triazolo[1,5-a]pyrimidine, potassium bicarbonate, sulfur, meptyldinocap, potassium phosphite, copper oxychloride, kasugamycin, 2,3-dimethyl-6-t-butyl-8-fluoro-4-acetylquinoline, 2-(2-fluoro-5-(trifluoromethyl)phenylthio)-2-(3-(2-methoxyphenyl)thiazolidin-2-yliden)acetonitrile, 4-(2,3,4-trimethoxy-6-methylbenzoyl)-2,5-dichloro-3-trifluoromethylpyridine, 4-(2,3,4-trimethoxy-6-methylbenzoyl)-2-chloro-3-trifluoromethyl-5-methoxypyridine, 3-(2,3,4-trimethoxy-6-methylbenzoyl)-5-bromo-4-chloro-2-methoxypyridine, 3-(2,3,4-trimethoxy-6-methylbenzoyl)-5-chloro-2-methoxy-4-methylpyridine, bixafen, fluopyram, and isopyrazam;
   wherein the blend weight ratio of (a) to (b) is from 1:1000 to 2083:1.

2. A method for controlling noxious fungi, which comprises applying the composition as defined in claim 1 to noxious fungi or to a site where noxious fungi grow.

3. A method for controlling noxious fungi, which comprises applying (a) the carboxylic acid amide derivative, and applying (b) the fungicidal compound, as defined in claim 1, to noxious fungi or to a site where noxious fungi grow.

\* \* \* \* \*